US005790627A

United States Patent [19]

Iketaki

[11] Patent Number: 5,790,627
[45] Date of Patent: Aug. 4, 1998

[54] METHOD AND APPARATUS FOR OBSERVING A SPECIMEN USING AN X-RAY MICROSCOPE

[75] Inventor: Yoshinori Iketaki, Ohme, Japan

[73] Assignees: Research Development Corp., Kawaguchi; Olympus Optical Co., Ltd., Tokyo, both of Japan

[21] Appl. No.: 717,180

[22] Filed: Sep. 20, 1996

[30] Foreign Application Priority Data

Sep. 20, 1995 [JP] Japan ................................. 7-241887
Oct. 9, 1995 [JP] Japan ................................. 7-261901

[51] Int. Cl.[6] ................................................. G21K 7/00
[52] U.S. Cl. ................................................ 378/43; 378/210
[58] Field of Search ................................................ 378/43

[56] References Cited

U.S. PATENT DOCUMENTS 5,107,526 4/1992 Hoover ................................. 378/43

*Primary Examiner*—Craig E. Church
*Attorney, Agent, or Firm*—Sherman and Shalloway

[57] ABSTRACT

X-ray microscopy is used to observe a specimen by labelling the specimen with a molecule having a double bond, such as, for example, N-succinimidyl-4-nitrophenyl acetate or 5-(dimethylamino phenyl)-2,4-pentadienal, which bond to an amino group, and O-(4-nitrobenzyl)-N,N-diisopropyl isourea, which chemically bonds to a carbonyl group. Such labelling groups can generate fluorescence to facilitate the observation of the specimen. Observation is improved by using a monochromatic X-ray source having a photon energy lower than 2000 eV and a band width narrower than 1 eV.

17 Claims, 5 Drawing Sheets

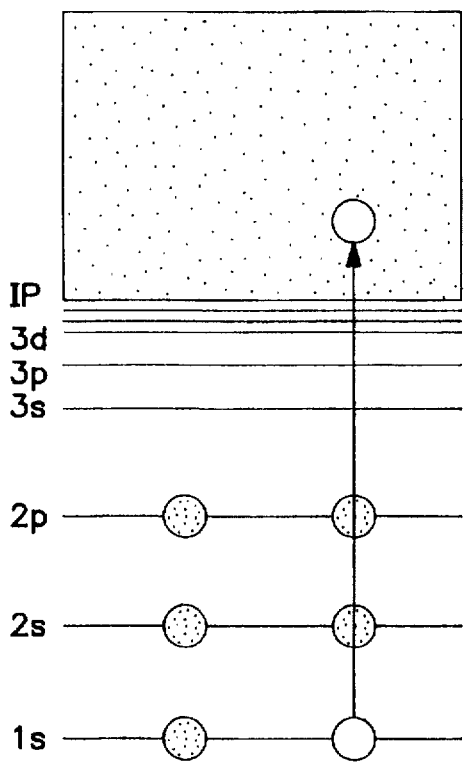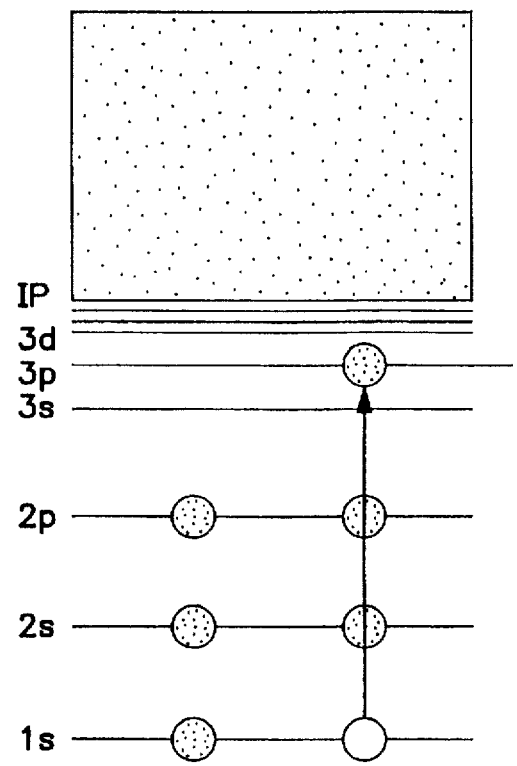
FIG. 4A
FIG. 4B
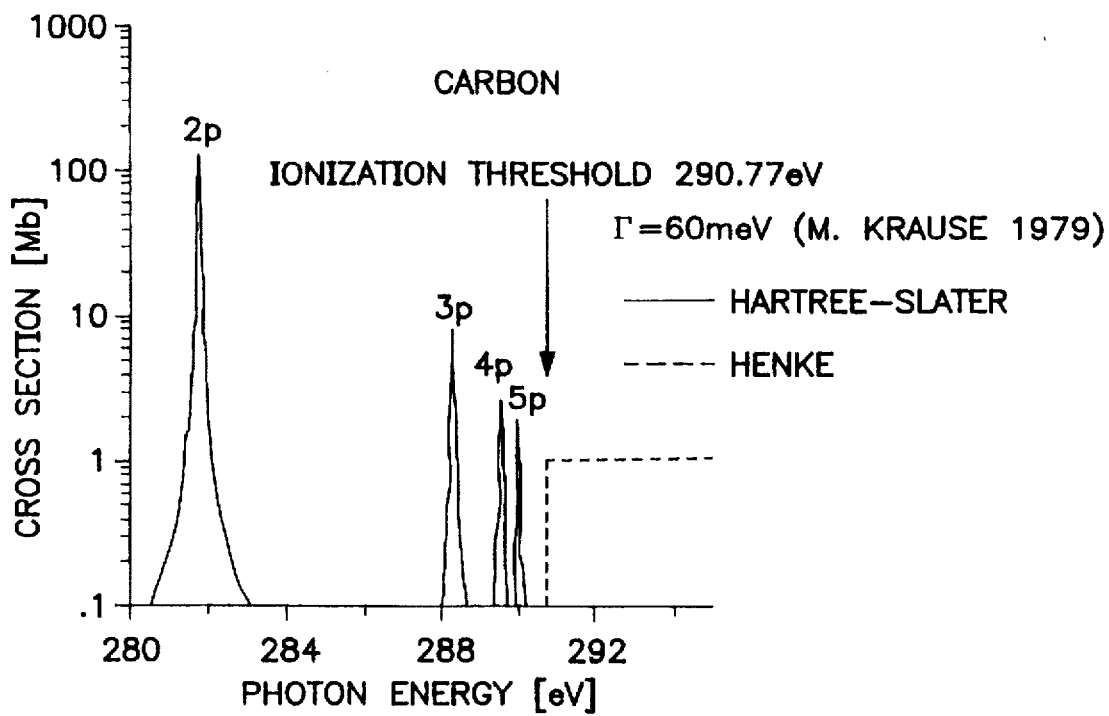
FIG. 5

METHOD AND APPARATUS FOR OBSERVING A SPECIMEN USING AN X-RAY MICROSCOPE

BACKGROUND OF THE INVENTION

This invention relates to a new and high functional X-ray microscope system and the use thereof for observing a sample.

DESCRIPTION OF THE PRIOR ART

Recently, technique of X-ray radiation sources and X-ray optic elements have been remarkably improved, and an X-ray microscopes is proposed as one of their applications. Several types of microscope can be mentioned as the substantial examples of such microscope. For instance, microscope systems using many types of imaging element such as a grazing incident X-ray optic elements represented by a Walter type shown in FIG. 1, a Fresnel zone plate using diffraction grating shown in FIG. 2 or, normal incident type Schwarzschild optic elements characterized by X-ray multiple film mirror is evaporated on two spherical mirrors shown in FIG. 3 have been developed. Furthermore, a direct contact photographing method is conventionally applied, which records an image of specimen directly on X-ray film or photo-resist without using optical elements.

Especially, X-ray is useful because it gives less damage to a biological specimen compared with an electronbeam, and so the X-ray microscopy is presently noted as a newly developed biological microscope which makes it possible to observe a biological specimen in wet condition by high resolving power without staining. Particularly, in the wavelength region from 42.7 to 23. 6Å, since X-ray has an absorption region by carbon or nitrogen atom and also has a high transmittance to a water molecule composed of oxygen and hydrogen, transmittance imaging of protein mainly composed with carbon atom can be observed by an excellent contrast even in water. This region of wavelength is called "the water window". 42. 7Å wavelength corresponds to the K absorption edge of carbon and 23.6 Å wavelength is corresponds to the K absorption edge of oxygen.

The photographing principle of X-ray absorption imaging is based on the inner shell photoionization process of 1s electrons of carbon and nitrogen atom. Up to the present time, this had been considered as a major principle, however, recently, following X-ray microscopy is proposed. That is, the microscopy which uses an inner shell photoexcitation process to a molecular orbit of biological molecule is proposed and is different from the said inner shell photo-ionization process. The wavelength of X-ray used in this case is slightly longer than the K absorption edge. The absorption process by the inner shell photoexcitation process corresponds to a resonance absorption, and the said X-ray microscopy has higher sensitivity than that of the microscopy using the inner shell photoionization process.

The principle of the inner shell photoionization process to a molecular orbit of biological molecule, and also the principle of X-ray microscopy using the inner shell photoexcitation process are illustrated by FIG. 4A and 4B. That is, FIG. 4A shows the X-ray microscopy using the inner shell photoionization process, wherein 1s electrons of carbon or nitrogen atom of a biological molecule are excited by using the X-ray of the wavelength of the "water window" region from 42. 7Å to 23. 6Å and obtain the photoabsorption imaging of X-ray. On the other hand, FIG. 4B is a drawing illustrating a principle of X-ray microscopy which uses inner shell photoexcitation process, wherein 1s electrons of carbon are excited by X-ray to an unoccupied molecular shell by electrons of biological molecule. This method is a kind of resonance photoabsorption process, and strong photoabsorption of X-ray can be expected [reference Y. Iketaki et al: Rev. Sci. Instrum. 66(1995)982]. Furthermore, since the said molecular orbit has the energy level specific to the molecule, photoabsorption imaging of a specific molecule alone can be observed by selecting a resonance wavelength of X-ray. Therefore, this method can be superior to the X-ray microscopy which uses the inner shell photoionization process.

The molecular orbit that plays an important part in the inner shell photoexcitation process is an antibonding molecular orbit, or so-called it $\pi$ orbit, and ordinarily is an unoccupied orbit. The said $\pi$ orbit can be frequently observed when the 2p orbit of carbon atom which composes a biological molecular is hybridized with orbits of an another atom. For instance, in the case of benzene ring or base including nitrogen, a strong absorption spectrum closely at 43.5 ∈(285 eV) wavelength of X-ray. The energy position of the absorption spectrum is located at the longer wavelength side about 1 Å beyond the limit of the "water window" region (about 5 eV lower energy side, when converted to the photon energy).

However, even if the X-ray microscopy is excellent, it become clear that there is a limit for its adaptation. That is, the biological molecular which can be observed are limited to benzene ring or the special molecules which include nitrogen base.

OBJECT OF THE INVENTION

The inventors have conduced intensive studies to extend the limit for adaptation of the conventional X-ray microscopy and to make it possible to observe the photoabsorption imaging of a selected chemical group in a biological cell, and found out that this object can be solved by using the photon energy of specific X-ray and by labelling said chemical group with the molecule having $\pi$ orbit which generates specific strong photoabsorption of soft X-ray. Consequently, the inventors have accomplished the present invention, and the object of this invention is to provide a new and high quality X-ray microscopy.

BRIEF SUMMARY OF THE INVENTION

The important point of this invention include, an X-ray microscopy characterized by using a monochromatic X-ray of lower photon energy than 2000 eV with a narrower band width than 1 eV, and characterized a method of observing a specimen by labeling the specimen with a molecule including double bond.

BRIEF DESCRIPTION OF DRAWINGS

FIG. 4A and 4B are schematic views illustrating inner ionization process and inner excitation process.

FIG. 5 is a graphic representation of photon energy and cross section when 1s electrons of carbon atom are excited to each p orbit.

DETAILED DESCRIPTION OF THE INVENTION

Figure 1:
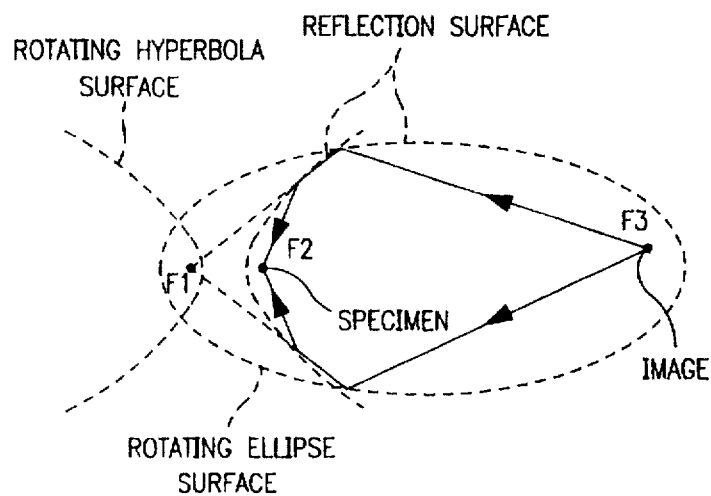
FIG. 1 is a schematic view illustrating an optical system of conventional Walter type X-ray microscope.
Figure 2:
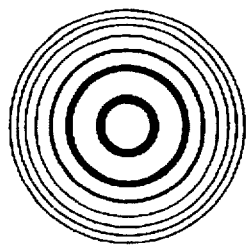
FIG. 2 is a front view of Fresnel zone plate.
Figure 3:
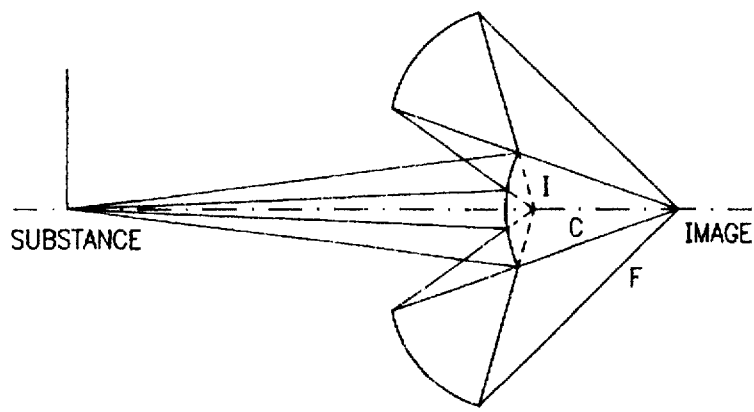
FIG. 3 is a schematic view illustrating Shwarzschild optical system.

The principle of this invention is illustrated below. In the field of fluorescent analytical chemistry or biology, the technique to label a specific chemical group of a biological cell molecular with a molecular having fluorescent group (hereafter these moleculars are referred to as labeller) and to analyze an organization or a composition of a biological cell by observing the fluorescence generated from the labelled molecular is remarkably progressed. For instance, N-Succinimidyl-4-nitrophenyl acetate or 5-(-Dimethylamino phenyl)-2,4-pentadienal is chemically bonded with amino group (N edge) of protein and generates strong ultra violet fluorescence light. And, O-(4-Nitrobenzyl)-N, N'-diisopropyl isourea is chemically bonded with carbonyl group (C edge) of protein and generates strong ultra violet fluorescence light. Further, N,N,N',N'-Tetrakis(2-phridylmethyl)ethylenediamine labels an information transferring material Ca2+ which plays an important part in a cell. In addition to these, 4-Fluroro-7-sulfobenzofurazan ammonium salt is chemically bonded, for instance, with SH group of cysteine which is a kind of an amino acid, and generates strong fluorescence of 515 nm at 385 nm excitation.

These molecules have a common feature that generate strong fluorescence, and the reason of said feature is originated in the structure of molecular orbit of these moleculars. That is, these moleculars have reliable chemical groups including double bond. And where there is a double bond, $\pi$ electrons exist. These electrons exist on the molecular orbit which is generally called as $\pi$ orbit, which is easily excited to the higher unoccupied $\pi$ orbit or to the antibonded $\pi$ orbit by ultra violet or visible light. And, due to the excited state, these electrons generate strong fluorescence when they are de-excited to the ground state.

In the meantime, considering about $\pi$ orbit or $\pi$ orbit from the view point of quantum chemical mechanics, these molecular orbits are generally formed by linear combinations of 2p orbit of atoms that compose a molecule. That is, $$\psi = \sum_{i=1}^{n} Ci\chi_i(r) \qquad (1)$$

Wherein, $\chi i(r)$ indicates the wave functions of 2p orbit of "i" th atom composing the molecule, and Ci indicates the normalization constant.

2p orbit of atom has a strong interaction with electrons on is orbit by photon excitation. That is, according to the quantum mechanics, the electrons on orbit have a high transition probability to 2p orbit in the case of photon excitation. Thereupon, in the case of carbon atom, the photoabsorption cross section of the transition of 1s orbit electrons to each p orbit and that of ionization of 1s orbit electrons are calculated, and the results are shown in FIG. 5 [reference Y. Iketaki et al Rev. Sci. Instrum. 66(1995)982].

According to FIG. 5, it is clearly understood that the photoabsorption cross section caused by the transition from 1s to 2p orbit is approximately 150 Mb ($150 \times 10^{-18}$ cm$^2$), which value is 100 times stronger compared with the photo-ionization of 1s electrons by using excitation at the wavelength of the "water window".

Generally, there is not an atomic orbit in a biological molecular, however, a molecular orbit composed by linear combinations of atomic orbits indicated by formula (1) exists. Consequently, the resonance photoabsorption caused by an inner shell photoexciting process comprising transitions of 1s electrons of atoms composing a molecular to the said molecular orbit becomes possible. From formula (1), it is understandable that the wave functions of $\pi$ orbit or $\pi$ orbit are given by linear combinations of 2p orbit of the atoms composing the molecular, and the photoabsorption cross section of transitions of 1s electrons of composing atoms such as carbon, nitrogen and oxygen to the unoccupied $\pi$ molecular orbit by electrons is slightly broad.

Figure 6:
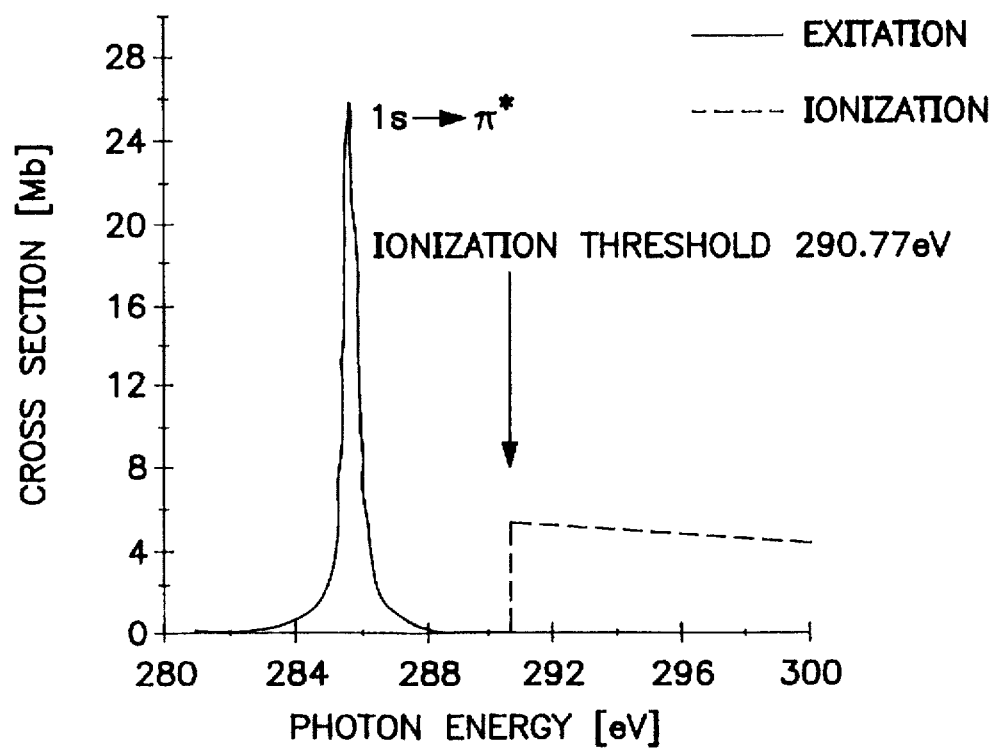
FIG. 6 s a graphic representation of photon energy and cross section when 1s electrons of benzene transit to $\pi$ molecular orbit.

FIG. 6 shows the results of calculation of the photoabsorption cross section assuming transitions of 1s electrons to each p orbit, in the case of hexagonal ring molecule such as benzene. From FIG. 6, it can be found that the cross section at 285 eV around photon energy is six times larger than that of 1s electrons ionization by using excitation wavelength of the "water window" region. Additionally, even if unless the hexagonal ring compound, any molecule having double chemical bond, generates very strong resonance photoabsorption by inner shell exciting process at slightly smaller photon energy region than the "water window" region (slightly longer wavelength than exciting wavelength of the "water window" region).

Since the labeller used in the fluorescent analysis includes a lot of double bond, it is clear from the view point of above mentioned argument that it acts as an absorption labeller for the soft X-ray having the wave length which generates an inner shell photo-exciting process. That is, only distributed image of the specific chemical group can be obtained by photographing a transmittance image of a biological specimen, by labelling specific chemical groups in a biological molecular represented by amino acid, and by using the resonating X-ray having the wavelength which generates an inner shell exciting process. Moreover, since the absorption by said resonance is very strong so as to detect the chemical groups of very small amount, in comparison with the conventional X-ray microscopy, an excellent high functional X-ray microscopy can be developed by introducing these kind of labelling technique.

For the realization of above mentioned principle, the following two necessary conditions must be satisfied. (1) A molecule including double bond is used as a labeller. (2) An X-ray is used, which has narrower band width wavelength (or photon energy width) than resonance line generates an inner shell exciting process that the labeller has.

When the application is limited to a biological microscope, the following additional condition is mentioned. (3) To photograph a wet specimen, X-ray must not be absorbed by a molecule of water.

Above mentioned three conditions are substantially discussed below.

Substantial discussion of (1).

In general, labeller is an organic molecular including mainly hydrogen, carbon, nitrogen or oxygen and small amount of sulfur, bromine or lead. Therefore, it is advantageous to use an absorption line when is electrons of carbon, nitrogen and oxygen are photoexcited to $\pi$ orbit or $\pi$ orbit of labeller. In the case of respective organic molecules, the photon energy (or wavelength) of respective organic molecules can be roughly presumed from the related literatures or the experimental papers. These are mentioned below.

(i) C: 1s→$\pi$ 280–300 eV (44Å–41Å)

(a) M. N. Piancastelli et al. J. Chem. Phys. 90(1989), 1987
(ii) N: 1s→π 390–410 eV (32Å–30Å)
(b) J. A. Horsley et al. J. Chem. Phys. 83(1985), 6099
(iii) O: 1s→π 520–550 eV (24Å–22Å)
(c) I.Ishii et al. J. Chem. Phys. 87(1987), 830
N.Kosugi et al. J. Chem. Phys. 97(1992), 8842

In the region above, many kinds of absorption peaks by inner shell excitation process including 1s →π can be observed. Moreover, in the case of heavy elements such as sulfur, bromine or lead, many kinds of absorption peaks from inner shell orbit, not only 1s→π but also 2P, 2s, 3S, 3P, 3d . . . are observed at under 2000 eV level. Therefore, the X-rays microscopy of this invention can be effectively applied, if the X-ray of above mentioned region is used.

Substantial discussion of (2).

According to the literatures of (a), (b) and (c), aiming at the strongest absorption peak along with 1s→π transitions, it has a line width of approximately 1 eV around. Therefore, it becomes an necessary condition to use a X-ray which has band width at least under 1 eV photon energy width. If the transmittance image is photographed by wider band width than the said width, the contrast of photograph is remarkably dropped because the wavelength which does not participate in absorption are mixed together. Consequently, it is important to use an optical element which has an excellent resolving power thinner than above mentioned band width and a wavelength dispersing ability , and to use a monochromatic light source.

Substantial discussion of (3).

For the purpose to photograph a wet specimen, it is a necessary condition that the X-ray is not absorbed by a molecule of water. That is, in this case, this means that it is necessary to use a soft X-ray having longer wavelength than k absorption edge of an oxygen atom in a molecular of water (longer wavelength region than 23. 6Å). Thus, by using the present principle, it becomes possible to develop a high functional soft X-ray microscopy which can distinguish specific chemical groups, and is superior to the conventional ones.

The present invention is illustrated in detail as follows.

The photon energy of X-ray used in the X-ray microscopy of this invention is smaller than 2000 eV and is characterized as the monochromatic X-ray having thinner width of wavelength than 1 eV. The reason why the photon energy of X-ray is settled lower than 2000 eV is illustrated as follows, that is, because the absorption peaks from 1s electron or from other inner shell orbits such as 2p, 2s, 3s, 3p or 3d are observed at lower energy than 2000 eV. And it is preferable that the photon energy of the X-ray is between 280 eV and 550 eV and is further preferable that the wavelength is variable.

To observe many kinds of biological molecule by the X-ray microscopy of this invention, the specimen of biological molecular is labelled by a molecular including double bond. 1s electrons of carbon, nitrogen and oxygen atoms which compose said biological molecular are photoexcited by labelling and absorbed to π. Photon energy of 280–550 eV X-ray is used for 1s→π absorption of carbon, nitrogen and oxygen atoms. Particularly, by using X-ray having 280–290 eV photon energy, it becomes possible to observe the absorption imaging when 1s electrons of carbon atom are transferred to π orbit. At this moment, since the photon energy of X-ray becomes smaller than the ionization energy of 1s electron of carbon atom, only shadow formed by π orbit can be purely photographed by S/N. Concretely, compounds including pentagonal or hexagonal ring, especially compounds including benzene ring are preferably used as the compound to dye a specimen. Furthermore, any compound used as a labeller in fluorescence analytical chemistry field can be used as the molecule to dye a specimen in this invention. These embodiments are shown below.

(1) labeller for thiol group (R-SH)

A molecular generates an exchange reaction of disulfide or arylhalide can be mentioned, characterized as a molecular having maleimide group utilize an unique reaction of SH group. For instance:

4-Fluoro-7-sulfamoylbenzofurazan 2,2-Dihydroxy-6,6'-dinaphthyl disulfide

N-(9-Acridinyl)maleimide (2) labeller for carboxyl group (R-COOH)

A molecular utilize promethyl group as a reaction activated group. For instance a 4-Bromomethyl-7-methoxycoumarin 3-Bromomethyl-6,7-dimethoxy-1-methyl-1,2-dityhydroquinoxalne -2-one (3) labeller for amino group (R-NH, R-NH$_2$)

A molecule utilize isothiocyanate group, ferrocenileisothiocyanate group, nitroallylhalide and acid-chloride group as an activated group. For instance Fluoresceinisothiothiocyanate,isomer-1

4-[4-(Dimethylamino)phenylazo]phenylisothiocyanate

4-Chloro-7-nitrobenzofurazan

4-Fluroro-7-nitrobenzofurazan

3-Chlorocarbonyl-6,7-dimethoxy-1-methyl-2(1H) quinoxalinone

N-Succinimidyl-4-nitrophenylacetate

Sulforhodamine 101 acid chloride (4) labeller for aldehyde group For instance:

1,2-Diamino-4,5-dimethoxybenzen, dihydrochloride 2,2'-Dithiobis(1-aminonaphthalene)

(5) labeller for hydroxyl group Acid chloride is utilized. For instance

3-Chlorocarbonyle-6,7-dimethoxy-1-methyl-2(1H) quinoxalinone (6) labeller for hydrophobic pocket of protein For instance:

3,6-Bis(dimethylamino)-10-dodecylacridinium bromide

4-Benzylamino-7-nitrobenzenzofurazaii 4-(4-Methoxybenzylamino)-7-nitrobenzofurazan (7) labeller for calcium ion in biological cell For instance:

0,0'-Bis(2-aminophenyl)ethyleneglycol-N,N,N',N'-tetraacetic acid, tetrapotassium salt, hydrate N,N,N',N'-Tetrakis(2-pyridylmethyl)ethylenediamine 1-[2-Amido-5-(2,7-dichloro-6-hydroxy-3-oxy-9-xanthenyl) phenoxy]-2-(2amino-5-methylphenoxy) ethane-N,N,N',N'-tetra acetic acid (8) labeller for pH in biological cell For instance:

2'7'-Bis(carboxyethyl)-4 or 5-carboxyfluorescein

3'-0-Acetyl-2',7'-bis(carboxyethyl)-4 or 5-carboxyfluoresceein,diacetoxymethyl ester (9) labeller for biological cell membrane (phospholipid, bio-membrane) For instance:

1,3-Bis(1-pyrenyl)propane 1-(4-Trimethylammoniumphenyl)-6-phenyl-1,3,5-hexatriene iodide

(10) labeller for nucleic acid represented by DNA For instance:

4'6-Diamino-2-phenylindole(DAPI)

And, in the case of the X-ray microscopy of this invention, an organic molecular or a carbonized composition which does not have π orbit is utilized as material for a window of a specimen container so as not to cause a reciprocal action with the specimen.

The present invention is illustrated by Examples.

EXAMPLES AND COMPARATIVE EXAMPLES

Example-1

The labelling method by using O-(4-Nitrobenzyl) hydroxyl amine hydrochloric acid salt is disclosed in this Example. This compound is indicated by following formula, and acts as a labeller by combining with ketone group or aldehyde group.

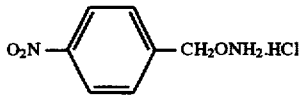

This compound includes benzene ring, and has a strong absorption peak of X-ray accompanied with carbon $1s \rightarrow \pi$ transition at photon energy of about 285 eV. In this example, the following labelling case is discussed, in which a tobacco mosaic virus is preferred as a typical concrete case and ketone group or aldehyde group of a protein molecular of the virus is labelled. The tobacco mosaic virus forms a rod like figure of 12×300 nm, and a protein of the virus composed by 2130 groups of protein small groups which is composed by 158 moleculars of amino acid. Each amino acid molecular includes one peptide bond which has ketone group or aldehyde group. Thus, one tobacco mosaic virus includes 158×2130 ketone groups or carbonyl groups. The strongest absorption value accompanied with $1s \rightarrow \pi$ transition when the ketone group or aldehyde group of the tobacco mosaic virus is labelled with O-(4-Nitrobenzyl)hydroxylamine is estimated as follows.

According to the literature which was published by the inventors of this invention (Y. Iketani et al: Rev. Sci. Instrum. 66[1995]982), absorption cross sectional area σ of one benzene molecule is about 25 Mb($25 \times 10^{-18}$ cm$^2$) and line absorption coefficient μ by inner shell excitation can be obtained by the product of σ and the density of ketone groups or aldehyde groups in one unit volume. The line absorption coefficient μ at the resonance wavelength of labelled tobacco mosaic virus is 13/μm. This value is almost two times as much as the line absorption coefficient of wavelength of "water window" region which a normal protein has.

The contrast "C" of microscope is defined by formula (2), wherein "Imax" is a maximum transmittance of specimen having various region of contrast and "T" is a transmittance of an object region.

$$C = \frac{Imax - I}{Imax + I} \quad (2)$$

The transmittance "T" of tobacco mosaic virus having X=16 nm size is defined as formula (3).

$$I = e^{-\mu x} \quad (3)$$

The contrast of tobacco mosaic virus is estimated to about 0.1. This value is two times as much as the value obtained by the conventional technique which uses the wavelength of the "water window". It is clearly understood that by using the technique of this invention, proteins can be detected with very high sensitivity.

Example-2

A specific chemical group, molecule and structure of biological cell can be discriminated by using a labeller molecule preferably from various types of molecules listed in Table 1 to Table 40 instead of O-(4-Nitrobenzyl) hydroxylamine which is used in Example-1.

Basically, a molecule which has a functional group and at least one double bond can fulfill the function of labeller of X-rays microscopy of this invention, unless utilizing a complicated molecule of various types of labeller molecules listed before.

Table 1
AA
ABD-F
ACES
N-(2-Acetamido)-2-aminoethanesulfonic acid
N-(2-Acetamido)iminodiacetic acid
Acetone(Sp)
Acetonitrile(Lu)
Acetonitrile(Sp)
Acetonitrile(NS)
8-Acetoxyquinoline
Acetylacetone
3'-O-Acetyl-2',7'-bis(carboxyethyl)-4 or 5-carboxyfluorescein, diacetoxymethyl ester
Acetylene derivatives
Acetyloxine
Acna Base V
Acridinium-I
N-(9-Acridinyl)maleimide
ADA
ADOS
ADPS
AEGT
Agarose-I(for electrophoresis)
Agarose-II(for electrophoresis)
Agarose-III(for electrophoresis)
Ag (I) -CHBA (AS)
Ag Diethyldithiocarbamate
Akiyama's Reagent
AL-1 (Sc)
Al(III)-AA
Albron
ALC
Alfusone$^R$ (ALC-La chelate+buffer)
ALOS
ALPS
Aliquat 336S
Alizarin Complexan
Alizarin Complexone
Alizarin fluorine blue
Alzarin-3-methyliminodiacetic acid
Aluminium acetylacetonate
ALX-2 (Sc)
AM-1 (Sc)
8-Amino-2-[(2-amino-5-methylphenoxy)methyl]-6-methoxyquinoline-N,N,N',N'-tetraacetic acid, tetrapotassium salt
8-Amino-2-[(2-amino-5-methylphenoxy)methyl]-6-methoxyquinoline-N,N,N',N'-tetraacetic acid, tetraacetoxymethyl ester
8-Amino-2-(trans-2-aminostyryl)-6-methoxyquinoline N,N, N',N'-tetraacetic acid, tetrapotassium salt
8-Amino-2-(trans-2-aminostyryl)-6-methoxyquinolineN,N, N',N'-tetraacetic acid, tetraacetoxymethyl ester
Table 2
Aminobenzyl-EDTA
1-(4-Aminobenzyl)ethylenediamine-N,N,N',N'-tetraacetic acid
1-[2-Amino-5-(6-carboxy-2-indolyl)phenoxy]-2-(2-amino-5-methylphenoxy)ethane-N,N,N',N'-tetraacetic acid, pentapotassium salt 1-[2-Amino-5-(6-carboxy-2-indolyl)phenoxy]-2-(2-amino-5-methylphenoxy)ethane-N,N,N', N'-tetraacetic acid, pentaacetoxymethyl ester 1-[6-Amino-2-(5-carboxy-2-oxazolyl)-5-benzofuranyloxy] 2-(2-amino-5-methylphenoxy)ethane-N,N,N',N'-tetraacetic acid, pentapotassium salt 1-[6-Amino-2-(5-carboxy-2-oxazolyl)-5-benzofuranyloxy] 2-(2-amino-5-methylphenoxy)ethane-N,N,N',N'-tetraacetic acid, pentaacetoxymethyl ester 1-[2-Amino-5-(2,7-dichloro-6-hydroxy-3-oxy-9-xanthenyl)phenoxy]-2-(2'-amino-5'-methylphenoxy)ethane-N,N,N', N'-tetraacetic acid 1-[2-Amino-5-(2,7-dichloro-6-hydroxy-3-oxy-9-xanthenyl)-phenoxy]-2-(2'-amino-5'-methylphenoxy)ethane-N,N, N',N'-tetraacetic acid, pentaacetoxymethyl ester 1-[2-Amino-5-(3-dimethylamino-6-dimethylammonio-9-xanthenyl)-phenoxy]-2-(2-amino-5-methylphenoxy)ethane-N,N,N',N'-tetraacetic acid, chloride 1-[2-Amino-5-(3-dimethylamino-6-dimethylammonio-9-xanthenyl)-phenoxy]-2-(2-amino-5-methylphenoxy)ethane-N,N,N',N'-tetraacetic acid, tetraacetoxymethyl ester, chloride 1-{2-Amino-5-[hydroxy(4,5-methylenedioxy-2-nitrophenyl)methyl]phenoxy}-2-(2-amino-5-methylphenoxy)-cyclopentane-N,N,N',N'-tetraacetic acid 1-{2-Amino-5-[hydroxy(4,5-methylenedioxy-2-nitrophenyl)methyl]phenoxy}-2-(2-amino-5-methylphenoxy)-ethane-N,N,N',N'-tetraacetic acid 4-Amino-4'-methoxydiphenylamine hydrochloride 3-Aminomethylalizarin-N,N-diacetic acid 2-(2-Amino-5-methylphenoxy)methyl-6-methoxy-8-aminoquinoline-N,N,N',N'-tetraacetic acid, tetrapotassium salt 2-(2-Amino-5-methylphenoxy)methyl-6-methoxy-8-aminoquinoline-N,N,N',N'-tetraacetic acid, tetraacetoxymethyl ester 4-Amino-3-penten-2-one 2-Aminoperimidine HBr 2-Amino-1H-perimidine, hydrobromide 2-Aminoperimidine HCl 2-Amino-1H-perimidine,hydrochloride 2-(trans-2'-Aminostyryl)-6-methoxy-8-aminoquinoline-N, N,N',N'-tetraacetic acid, tetrapotassium salt 2-(trans-2'-Aminostyryl)-6-methoxy-8-aminoquinoline-N, N,N',N'-tetraacetic acid, tetraacetoxymethyl ester 4-Amino-4'-sulfopropylamino-3,3',5,5'-tetramethylbiphenyl, sodium salt Ammonium 7-fluorobenzo-2-oxa-1,3-diazole-4-sulfonate Table 3

Ammonium purpurate

Arsenic acid-N,N,N',N'tetraacetic acid

Anisidine Blue$^R$

Antarane X 230

Antra

AO-10-Dodecyl bromide

APANS

Aqunasol$^R$

Arsemate$^R$

Arsenazo

Arsenazo-I

Arsenazo-III

Arsenazo K p-{[p-[3(2-Arsono-4-nitrophenyl)2-triazeno]phenyl]azo}benzensulfonic acid, sodium salt 4'(2"-Arsono-4"-nitrophenylazoamino)azobenzene-4'-sulfonic acid, sodium salt 2-(2-Arsonophenylazo)-7-(2-carboxyphenylazo)-1,3-dihydroxy-3,6-naphthalenedisulfonic acid 3-(2-Arsonophenylazo)-4,5-dihydroxy-2,7-naphthalene disulfonic acid, disodium salt o-Arsonophenylazochromotropic acid: disodium salt 1-(2-Arsonophenylazo)2-naphthol-3,6-disulfonic acid, disodium salt Atlas G-3360

4-Azidofluorescein diacetate

Azido-FDA

Azobenzene derivatives

1-Azo-2-hydroxy-3-(2,4-dimethylcarboxanilido)naphthalene-1'-(2-hydroxybenzene)

1-Azo-2-hydroxy-3-(2,4-dimethylcarboxanilido)naphthalene-1'-(2-hydroxybenzene-5-sulfonic acid), sodium salt Azomethine H Ba (II)-CHBA (AS)

Ba(II)-EDTA

BAPTA

BAPTA-AM

Barium chloranilate

Bathocuproine

Bathocuproinedisulfonic acid, disodium salt

Bathophenanthroline

Bathophenanthrolinedisulfonic acid, disodium salt

BBD

BCECF

BCECF-AM

BDC-OH

Benzalkonium chloride

Benzene(CV)

Benzene(Sp)

Benzene(Pr)

Benzene(Lu)

Table 4

Benzenearsonic acid

Benzenearsonic(2)acid-(1-azo-1)-2-(hydroxynaphthalene)-3,6-disulfonic acid, disodium salt Benzol(Sp)

Benzol(Pr)

Benzol(Lu)

2-(2-Benzothiazolylazo)-5-dimethylaminobenzoic acid

4-Benzylamino-7-nitrobenzofurazan

7-Benzylamino-4-nitrobenzoxadiazole

Benzyldimethyltetradecylammonium chloride

Benzyldimethyl-{2-[2-(4-(1,1,3,3-tetramethylbutyl)-tolyloxy)ethoxyethyl}ammonium hydroxide N-Benzoyl-N-(2-methylphenyl)hydroxylamine N-Benzoyl-N-(2-tolyl)hydroxylamine Benzoyltrifluoroacetone

BES

BFA

BG

BHBT 2,2'-Bibenzoxazoline

Bicinchoninic acid

Bicinchoninic acid, disodium salt

Bicine

Bi-EDTA

Bifunctional Reagents

BIGCHAP

Bindschedler's Green, leuco base

Biotin Labeling Reagents

Biphenyl sodium 1M in diglyme (packed in vial)

Biphenyl sodium solutio 3,3'-(1,1'-Biphenyl-4,4'-diyl)-bis(2,5-dipheny-2H tetrazolium chloride)

3,3',4,4'-Biphenyltetramine hydrochloride 2-(4-Biphenylyl)-5-(4-tert-butylphenyl)-1,3,4-oxadiazole
2,2'-Bipyridine:α,α'-Bipyridine
1,2-Bis(2-aminoethoxy)ethane-N,N,N',N'-tetraacetic acid
O,O'-Bis(2-aminoethyl)ethyleneglycol-N, N, N', N'-tetraacetie acid
1,2-Bis(2-amino-4-fluorophenoxy)ethane-N,N,N',N'-tetraacetic acid
1,2-Bis(2-amino-4-fluorophenoxy)ethane-N,N, N',N'-tetraacetic acid, tetraacetoxymethyl ester
1,2-Bis(o-aminophenoxy)ethane-N,N,N',N'-tetraacetic acid tetraacetoxymethyl salt
1,2-Bis(2-aminophenoxy)ethane-N,N,N',N'-tetraacetic acid, tetraacetoxymethyl ester
O,O'-Bis(2-aminophenyl)ethyleneglycol-N,N,N',N'-tetraacetic acid, tetraacetoxymethyl ester
4,4'-Bis(4-anilino-6-dhydroxyethyl amino-s-triazine-2-ylamino)-2,2'-stilbenedisulfonic acid, disodium salt
4,4'-Bis(4-anilino-6-diethylamino-s-triazine-2-ylamino-2,2'-stilbenedisulfonic acid, disodium salt
Table 5
4,4'-Bis(4-anilino-6-methoxy-s-triazine-2-ylamino)-2,2'-stilbenedisulfonic acid, disodium salt
2,7-Bis(2-arsonophenylazo)chromotropic acid
2,7-Bis(2-arsonophenylazo)-1,8-dihydroxy-3,6-naphthalenedisulfonic acid
3,6-Bis[(o-arsonophenyl)azo]-4,5-dihydroxy-2,7-naphthalenedisulfonic acid
2,7-Bis(azo-2)-phenylarsono-1,8-dihydroxynaphthalene-3,6-disulfonic acid
2,7-Bis(azo-2)-phenylsulfo-1,8-dihydroxynaphthalene-3,6-disulfonic acid, tetrasodium salt
Bis(benzo-15-crown-5)
Bis[(benzo-15-crown-5)-4'-methyl]pimelate
3,3'-Bis{[bis(carboxymethyl)amino]methyl}phenolphthalein
3,3'-Bis[bis(carboxymethyl)aminomethyl]phenolphthalein
3'3"-Bis([bis(carboxymethyl)amino]methyl)-o-cresolsulfonphthalein. disodium salt
3'3"-Bis([bis(carboxymethyl)amino]methyl)-5',5"-dimethyl phenolphthalein
3'3"-Bis{[bis(carboxymethyl)amino]methyl}-5',5"-diisopropyl-2',2"-dimethylphenolphthalein
2',7'-Bis{(bis(carboxymethyl)amino]methyl}-7-hydroxy-4-methyl coumarin
3,3'-Bis(N-carboxymethylaminomethyl)thymolsulfonphthalein
[3-{3-(Bis(carboxymethyl)amino]-methyl-4-hydroxy-5-methyl-α-(o-carboxyphenyl)benzylidene}-5-methyl-6-oxo-1,4-cyclohexadien-1-yl]methyliminodiacetic acid
3,3'-Bis[N,N'-bis(carboxymethyl)aminomethyl]fluorescein
3,3'-Bis[N,N'-di(carboxymethyl)aminomethyl] thymolphthalein
3,3'-Bis[N,N'-bis(carboxymethyl)aminomethyl]-thymolsulfonphthalein, disodium salt
3,3'-Bis[N,N'-bis(carboxymethyl)aminomethyl]-p-xylenolsulfonphthalein, tetrasodium salt
4,4'-Bis{[6-(N,N-diethylamino)-4-phenylamino-1,3,5-triazin-2-yl]amino}-2,2'-stilbenedisulfonic acid, disodium salt
Bis(12-crown-4)
Bis[(12-crown-4)methyl]-2,2-dibenzylmalonate
Bis[(12-crown-4)methyl]-2,2-didodecylmalonate
Bis[(12-crown-4)methyl]-2-dodecyl-2-methylmalonate
Bis[(15-crown-5)methyl]-2-dodecyl-2-methyl malonate
4,4'-Bis[(3,4-dihydroxyphenyl)azo]-2,2'-stilbenedisulfonic acid,diammonium salt
α,α-Bis(3,4-dihydroxyphenyl)-α-hydroxyo-o-toluenesulfonic acid, γ-sultone
4,4'-Bis(dimethylamino)benzhydrol
4,4'-Bis(dimethylamino)diphenylamine
2,8-Bis(dimethyamino)-10-dodecylacridinium bromide
Bis[di-(p-(1,1,3,3-tetramethylbutyl)phenyl)phosphato] calcium(II)
N,N-Bis(3-D-gluconamidopropyl)cholamide
N,N-Bis(3-D-gluconamidopropyl)deoxycholamide
Table 6
8-[N,N-Bis(carboxymethyl)aminomethyl]-4-methyl-umbelliferone
3'3"-Bis{(bis(carboxymethyl)amino]-methyl}-thymolsulfonphthalein
4,4'-Bis[{6-[N,N-bis(2-hydroxyethyl)amino]-4-phenylamino-1,3,5-triazin-2-yl} amino]-2,2'-stilbenedisulfonic acid, disodium salt
2',7'-Bis(carboxyethyl)-4 or5-carboxyfluorescein
3-[N,N-Bis(carboxyethyl)aminomethyl]1,2-dihydroxyanthraquinone
3',3"-Bis[N-(carboxymethyl)-N-methylaminomethyl]-o-cresolsulfonphthalein sodium salt
5,5'-Bis[(carboxymethyl)methylaminomethyl]-o-cresolsulfonphthalein,sodium salt
Bis(3-carboxy-4-nitrophenylsulfide)
2,7-Bis(4-chloro-2-phosphono-1-phenylazo)chromotropic acid, disodium salt
2,7-Bis(4-chloro-2-phosphono-1-phenylazo)1,8-dihydroxy-3,6-naphthalenedisulfonic acid, disodium salt
Bis[2-(5-chloro-2-pyridylazo)-5-diethylaminophenolato]-Co(III) chloride
3,3'-Bis[N,N'-di(carboxymethyl)aminomethyl]-o-cresolphthalein
3,3'-Bis[N,N'-di(carboxymethyl)aminomethyl]-o-cresolsulfonphthalein, disodium salt
3-[N,N-Bis(2-hydroxyethyl)amino]-2-hydroxypropanesulfonic acid
Bis[di n-octylphenyl)phosphato]calcium(II)
1,2-Bis(2-furyl)ethanedione dioxime, monohydrate
N,N'-Bis(2-hydroxybenzyl)ethylenediamine-N,N'-diacetic acid
N,N-Bis(2-hydroxyethyl)-2-aminoethanesulfonic acid
N,N-Bis(2-hydroxyethyl)glycine
3-[N-Bis(hydroxyethyl)amino]-2-hydroxypropanesulfonic acid
Bis(2-hydroxyethyl)iminotris(hydroxylmethyl)methane
2,2'-Bis(hydroxymethyl)-2,2',2"-nitrilotriethanol
Bis(2-hydroxy-6-naphthyl)disulfide
N,N-Bis(o-hydroxyphenyl)ethylenediimine
2,7-Bis(2-hydroxy-3-sulfo-5-chlorophenylazo)-1,8-dihydroxy naphthalene-3,6-disulfonic acid, tetrasodium salt
4,4'-Bis[(6-methoxy-4-phenylamino-1,3,5-triazin-2-yl)amino]-2,2'-stilbenedisulfonic acid, disodium salt
3,3'-Bis[N-methyl-N-carboxymethyl)aminomethyl]o-cresolsulfonphthalein, sodium salt
1,4-Bis(4-methyl-5-phenyl-2-oxazolyl)benzene
1,4-Bis(2-methylstyryl)benzene
p-Bis(o-methylstyryl)benzene
Bis-MSB(Sc)
2,7-Bis(4-methyl-2-sulfophenylazo)-1,8-dihydroxy-3,6-naphthalenedisulfonic acid, disodium salt
3,6-Bis(4'-methyl-2'-sulfophenylazo)-4,5-dihydroxy2,7-naphthalenedisulfonic acid, disodium salt
Table 7
Bismuthiol-II
Bis(4-nitro-2-sulfophenyl)disulfide-3,3'-dicarboxylic acid
2,7-Bis(4-nitro-2-sulfophenylazo)chromotropic acid, tetrasodium salt 2,7-Bis(4-nitro-2-sulfophenylazo)-1,8-dihydroxy-naphthalene-3,6-disulfonic acid, tetrasodium salt
3,6-Bis[(4-nitro-2-sulfophenyl)azo]-4,5-dihydroxy-2,7-naphthalenedisulfonic acid, tetrasodium salt
Bis(4-n-octylphenyl)phosphate, calcium salt
1,4-Bis(5-phenyl-2-oxazolyl)benzene
1,3-Bis(1-pyrenyl)propane
N,N'-Bissalicylidene-2,3-diaminobenzofuran
2,7-Bis(2-sulfophenylazo)chromotropic acid, tetrasodium salt
2,7-Bis(2-sulfophenylazo)-1,8-dihydroxy-3,6-naphthalenedisulfonic acid, tetrasodium salt
Bis[4-(1,1,3,3-tetramethylbutyl)phenyl]phosphate, calcium salt
Bis-Tris
Blue Base Irga VB
$BNBAC_3$-OSu
$BNBAC_3$ sulfo-OSu
$BNBAC_5$-OSu
$BNBAC_5$ sulfo-OSu
BNBA-OSu
BPA
BPHA
BPR
Br-DMEQ
Brenzkatechin-3,5-disulfonsaure, Dinatrium salz
Brenzkatechinviolett
Br-Mmc
2-Bromo-1-(4-bromophenyl)ethanone
3-Bromomethyl-6,7-dimethoxy-1-methyl-1,2dihydroquinoxaline-2-one
3-Bromomethyl-6,7-dimethoxy-1-methyl-2(1H)-quinoxalinone
4-Bromomethyl-7-methoxy-2H-1-benzopyrane-2-one
4-Bromomethyl-7-methoxycoumarin
p-Bromophenacyl bromide
2-[(5-Bromo-2-pyridyl)azo]-5-[N-propyl-N-(3-sulfopropyl)amino]aniline, sodium salt
2-[(5-Bromo-2-pyridyl)azo]-5-[N-propyl-N-(3-sulfopropyl)amino]phenol, sodium salt
Bromopyrogallol Red
5-Br-PADAB
5-Br-PAPS
5-Br-PSAA
BT
BT (Standard)
BTA
BTAMB
iso-Butyl alcohol(Sp)
iso-Butyl alcohol(Lu)
Butyl-PBD(Sc)
2-(4'-tert-Butylphenyl)-5-(biphenyl)-1,3,4-oxadiazole
Table 8
Ca (II) -AA
Ca(II)-EDTA
Caged Aspartic acid
Caged ATP
Caged ATP dimethoxy
Caged Calcium
Caged fluorescein
Caged cAMP
Caged cGMP
Caged compounds
Caged Fluorescein Dipalmitoylphosphatidylethanolamine
Caged Fluorescein maleimide
Caged Fluorescein OSu
Caged Fluoresc-ein sulfo-OSu
Caged GABA
Caged GDP
Caged-GDP dimethoxy
Caged Glutamic acid
Caged Glycine
Caged GTP
Caged GTP dimethoxy
Caged H'
Caged neurotransmitters
Caged Nucleotides
Caged Proton dimethoxy
Calcium acetylacetonate
Calcein
Calcein Blue
Calces
Calcichrome
Calcein IREA
Calciumrot
Calcofluor White ST
Caclofluor White M2R
Calcofluor carboxylic acid
Calmagite
Cal Red
Cal Ver I
Capriquat$^r$
Caproyl sucrose
CAPS
CAPSO
N- (Carbamoylmethyl)taurine
N- (Carbamoylmethyl)iminodiacetic acid
Carboxyarsenazo
4-(3-Carboxy-2-hydroxynaphthylazo)-3-hydroxy-1-naphthalenesulfonic acid
5or6-(N-Carboxymethylcarbamoyl)-3',6'-O,O-bis(2-nitrobenzyl)fluorescein
{[(Carboxymethyl)imino]bis(ethylenenitrilo)}tetraacetic acid
2-Carboxy-2'-hydroxy-5'-sulfoformazylbenzene, sodium salt
Table 9
N-(Carboxymethyl)-N'-(2-hydroxyethyl)-N,N'-ethylenediglycine
5-[(3-Carboxy-5-methyl-4-oxo-2,5-cyclohexadien-1-ylidene)(2,6-dichlorophenyl)methyl]-2-hydroxy-3-methylbenzoic acid, disodium salt
5-[(3-Carboxy-5-methyl-4-oxo-2,5-cyclohexadien-1-ylidene)2,6-dichloro-3-sulfobenzyl]-2,3-cresotic acid, sodium salt
2-(2-Carboxyphenylazb)-7-(2-arsonophenylazo) chromotropic acid
5-(2-Carboxyphenyl)-1-(2-hydroxy-5-sulfophenyl)3-phenylformazan, sodium salt
2-(4-Carboxyphenyl)-4,4,5,5-tetramethylimidazoline-1-oxyl 3-oxide
Carboxy-PTIO
Cd (II) -CHBA (AS)
Cd-cyclohexanebutyrate(for atom, absorp, standard)
CDTA
CDTA(for amino acid analysis)
Cell Biology
Cell Counting Kit
Cesibor
Ce(III)-AA
Cerium acetylacetonate
CFSE
CHAPS
CHAPSO CHBA
CHES
Chelating Reagents
Chelaton-I
Chelaton-III
Chelon 80
Chelon 100
Chelon 120
Chelon DHG
Chenta acid
Chloranilic acid
3-Chlorocarbonyl-6,7-dimethoxy-1-methyl-2(1H)-quinoxalinone
2-(5-Chlorocarbonyl-2-oxazolyl)-5,6-methylenedioxybenzofuran
4-Chloro-6-(2,4-dihydroxyphenylazo)-1-hydroxybenzene-2-sulfonic acid
5-Chloro-3-[(2,4-dihydroxyphenyl)azo]-2-hydroxybenzenesulfonic acid
Chloroform(Sp)
Chloroform(Lu)
5-Chloro-2-hydroxy-3-(2,4-dihydroxyphenylazo)benzenesulfonic acid
1-(5-Chloro-2-hydroxyphenylazo)-2-naphthol
Chlorohydroxyphenylazonaphthol
4-Chloro-7-nitrobenzofurazan
7-Chloro-4-nitrobenzoxadiazole
Chlorosulfophenol S
Table 10
Chlorophosphonazo-III
2-[5-Chloro-2-pyridinyl)azo]-5-(diethylamino)phenol
2-[5-Chloro-2-pyridinyl)azo]-5-(diethylamino)phenol, Co(III)compex
2-(5-Chloro-2-pyridylazo)-5-diethylaminophenol, Co(III) complex
2-(5-Chloro-2-pyridylazo)-5-diethylaminophenol
4-Chloro-7-sulfobenzofurazan, ammmonium salt
Chol-AECM-Mannan
Chol-AECM-Pullulan
3[(3-Cholamidopropyl)dimethylammonio]propanesulfonic acid
3[(3-Cholamidopropyl)dimethylammonio]-2-hydroxypropanesulfonic acid
{N-[2-(Cholesterylcarboxyamino)ethyl]carbamylmethyl}mannan
{N-[2-(Cholesterylcarboxyamino)ethyl]carbamylmethyl}pullulan
Chromazurol B
Chromazurol S
Chromic acetylacetonate
Chromic acetylacetonate, (for atom. absorp. standard)
Chromogen Black ET(C.I.14645)
Chromotail$^R$
Chromotropic acid
N-Cinnamoyl-N-phenylhydroxylamine
CLB
5-Cl-PADAP
Co(II)-AA
Co(III)-AA
Cobaltic acetylacetonate
Cobaltous acetylacetonate
Co (II) -CHBA (AS)
Co-5-Cl-PADAP
Co(II)cyclohexylbutyrate(for atom. absorp. standard)
Co(II)-EDTA
CPA
Cr(III)-AA
Cr(III)-AA(AS)
Cr(III)AA(for atom. absorp. standard)
Cr-trisacetylacetonate(for atom. absorp. standard)
Creatine phosphate
o-Cresolphthalein-3,3'-bismethyliminodiacetic acid
o-Cresolphthalein complexone
o-Cresolphthalexon S
o-Cresolsulfonphthalein-3,3'-bis(methylaminodiacetic acid), disodium salt
Cu(II)-AA
Cu(II)-AA(AS)
Table 11
Cu(II)-CHBA(AS)
Cu cyclohexanebutyrate
Cu cyclohexylbutyrate
Cu(II)-EDTA
Cu-PAN
Cu-bisacetylacetonate(for atom. absorp. standard)
Cupric acetylacetonate
Cupric acetylacetonate(for atom. absorp. standard)
Cyanoline Blue$^R$
Cyclo(D-Asn(Oct)$_2$-Pro-Ala)$_2$
Cyclo(N,N'-dioctyl-D-asparaginyl-L-prolyl-L-alanyl)$_2$
Cyclohexane(Sp)
Cyclohexane(Lu)
1,2-Cyclohexanediaminetetraacetic acid
1,2-Cyclohexanediaminetetraacetic acid (for amino acid analysis)
2-(Cyclohexylamino)ethanesulfonic acid
N-Cyclohexyl-2-aminoethanesulfonic acid
Cyclohexylaminopropanesulfonic acid
N-Cyclohexyl-3-aminopropanesulfonic acid
(1,2-Cyclohexylenedinitrilo)tetraacetic acid
N-Cyclohexyl-2-hydroxy-3-aminopropanesulfonic acid
Cyclo-tris-7-(1-azo-8-hydroxy-naphthalene-3,6-disulfonic acid), hexasodium salt
CYDTA
CyDTA(for amino acid analysis)
Cyquest 40
Cyquest Acid
Cyquest DEG
Cyquest 30-He
Detergent Starter Kit II
DAB
DABITC
Dabersen
DAMC(Laser dye)
DAMP-HCl
DAN
DAOS
DAPDA
DAPS
DBPH
DBPM
DCTA
DDB
DDD
DDI(Laser dye)
DDPC
Deblocking Reagents
n-Decanoyl-N-methylglucamide
deoxy-BIGCHAP
Table 12
Detergent Starter Kit
Detergent Starter Kit II
Detergehts
DHEG 3,3'-Diaminobenzidine tetrahydrochloride
1,3-Diamino-4-[5-bromo-2-pyridylazo]benzene
trans-1,2-Diaminocyclohexane-N,N,N',N'-tetraacetic acid
1,2-Diamino-4,5-dimethoxybenzene, dihydrochloride
4,4'-Diamino-3,3'-dimethoxybiphenyl-N, N, N',N'-tetraacetic acid, tetrasodium salt
Diaminoethanetetraacetic acid disodium salt
1,2-Diamino-4,5-methylenedioxybenzene dihydrochloride
2,3-Diaminonaphthalene
1,3-Diamino-2-hydroxypropane-N,N,N',N'-tetraacetic acid
1,2-Diaminopropane-N,N,N',N'-tetraacetic acit
4,4'-Diaminostilbene-2,2'-disulfonic acid-N,N,N',N'-tetraacetic acid disodium salt
o-Dianisidine-N,N'-tetraacetic acid, tetrasodium salt
3,3'-Dianisole-bis[4,4'-(2,5-diphenyl)tetrazolium chloride]
3,3'-Dianisole-bis[4,4'-[2-(p-nitrophenyl)-5-phenyl)tetrazolium-chloride]
Diantipyrylmethane
4,4'-Diantipyrylmethane, monohydrate
2,7-Di(o-arsonophenylazo)-1,8-dihydroxynaphthalene-3,6-disulfonic acid
Dibenzyl-Bis(12-crown-4)
Dibenzyl-14-crown-4
6,6-Dibenzyl-1,4,8,11-tetraoxacyclotetradecane
3,5-DiBr-PADAP
3,5-DiBr-PAESA
6,6-Dibenzyl-1,4,8,11-tetraoxacyclotetradecane
3,5-DiBr-PAMB
2,4-Dibromoacetophenone
2-[(3,5-Dibromo-2-pyridinyl)-azo]-5-(diethylamino)phenol
2-(3,5-Dibromo-2-pyridylazo)-5-diethylaminobenzoic acid
2-[(3,5-Dibromo-2-pyridinyl)-azo]-5-(diethylamino)benzoic acid
2-(3,5-Dibromo-2-pyridylazo)-5-diethylaminophenol
5,5'-Dibromopyrogallol-sulfonphthalein
3,3'-Dibromosulfongallein
o-(2,7-Dibromo-4 5,6-trihydroxy-3-oxo-3H-xanthen-9-yl)benzenesulfonic acid
4,4'-Dicarboxy-2,2-biquinoline disodium salt
3,3'-Di(N-carboxymethylaminomethyl)-thymolsulfonphthalein
Dichloro-CFSE
2,5-Dichloro-3,6-dihydroxy-p-benzoquinone
2,5-Dichloro-3,6-dihydroxy-p-benzoquinone barium salt, trihydrate
2,6-Dichloro-4'-hydroxy-3',3"-dimethylfuchsone-5',5"-dicarboxylic acid, disodium salt
Table 13
1,2-Dichloroethane(Sp)
Dichloromethane(Sp)
2,6-Dichloro-4'-hydroxy-3',3"-dimethyl-3-sulfofuchsone-5',5"-dicarboxylic acid, disodium salt
2,6-Dichloro-N-(4-hydroxyphenyl)-p-benzoquinoneimine, sodium salt
2,6-Dichlorophenolindophenol
DIDS
Didodecyl-bis(12-crown-4)
6-[2-(Diethoxyphosphoryloxy)ethyl]-6-dodecyl-1,4,8,11-tetraoxacyclotetradecane
7-Diethylaamino-4-methylcoumarin
1,1'-Diethyl-2,2'-dicarbocyanine iodide
Diethyldithiocarbamic acid, silver(I)
Diethylenetriamine-N,N,N',N",N"-pentaacetic acid
Diethyl ether(Aq)
Diethyl ether (AV. POV)
3,3'-Diethyloxacarbocyanine iodide
3,3'-Diethyloxadicarbocyanine iodide 4-(N,N-Diethylsulfamyl)-2-aminoanisolediazonium chloride, zinc double salt
4-(N,N-Diethylsulfamyl)-2-methoxybenzenediazonium chloride, zinc chloride double salt
3,3'-Diethylthiacarbocyanine iodide
3,3'-Diethylthiadicarbocyanine iodide
3,3'-Diethylthiatricarbocyanine iodide
Di-2-furylglyoxal dioxime
Diglyme(Sc)
3,4-Dihydro-6,7-dimethoxy-4-methyl-3-oxoguinoxaline2-carbonyl chloride
1,2-Dihydroxyanthraquinone-3-yl-methylamine-N,N-diacetic acid
(3,3-Dihydroxy-2-anthraquinoryl)iminodiacetic acid
{[(3,4-Dihydroxy-2-anthraquinoryl)methyl]iminoldiacetic acid
o,o'-Dihydroxyazobenzene
1,2-Dihydroxybenzene-3,5-disulfonic acid, disodium salt
4,5-Dihydroxy-m-benzenedisulfonic acid, disodium salt
4,5-Dihydroxy-3,6-bis[(2-sulfo-4-methylphenyl)azo]2,7-naphthalenedisulfonic acid, disodium salt
o-(1,8-Dihydroxy-3,6-disulfonaphthalene-2,7-bisazo)bis(benzenearsonic acid)
2-(4,5-Dihydroxy-2,7-disulfo-3-naphthylazo)benzenearsonic acid, disodium salt
4,5-Dihydroxy-3,6-bis[(o-sulfophenyl)-azo]-2,7-naphthalenedisulfonic acid, tetrasodium salt
2,2'-Dihydroxy-6,6'-dinaphthyldisulfide
2,2'-[-Dihydroxy-3,6-disulfo-2,7-naphthalenebis(azo)]dibenzene arsonic acid
N,N-Di(2-hydroxyethyl)glycine
Table 14
[(3,6-Dihydroxy-2,7-fluorandiyl)bis(methylene-nitrilo)]-tetraacetic acid
2, 8-Dihydroxy-1-(8-hydroxy-3, 6-disulfonaphthylazo)-3, 6-naphthalenedisulfonic acid, tetrasodium salt
1, 8-Dihydroxy-3,6-naphthalenedisulfonic acid, disodium salt
4, 5-Dihydroxy-2,7-naphthalenedisulfonic acid, disodium salt
1, 2-Di(o-hydroxyphenylimino)ethane
1, 8-Dihydroxy-2-(2-pyridylazo)-3, 6-naphthalenedisulfonic acid
4, 5-Dihydroxy-3-[(4-sulfophenyl)azo]-2, 7-naphthalenedisulfonic acid, trisodium salt
4, 4'-Diisothiocyano-2, 2'-stilbenedisulfonic acid, disodium salt
β-Diketones
threo-1, 4-Dimercapto-2, 3-butandiol
Dimercaptosuccinic acid
3, 3'-Dimethoxybenzidine-N, N, N', N'-tetraacetic acid, tetrasodium salt
[4-(5, 6-Dimethoxy-2-benzothiazolyl)phthalylhydrazide]
3, 3'-[3, 3'-Dimethoxy-(1, 1'-biphenyl)-4, 4'-diyl]-bis[2, 5-diphenyl-2H tetrazolium chloride]
3, 3'-[3, 3'-Dimethoxy-(1, 1'-biphenyl)-4, 4'-diyl]-bis[2-p-nitrophenyl)-5-phenyl-2H tetrazolium chloride]
[3, 3'-Dimethoxy-4, 4'-biphenylylene)dinitrilo]tetraacetic acid, tetrasodium salt
Dimethoxyethane(Sc)
4, 5-Dimethoxy-1, 2-diaminobenzene, dihydrochloride
5, 6-Dimethoxy-2-(4-hydrazinocarbonylphenyl)benzothiazole
6, 7-Dimethoxy-1-methyl-2(1H)-quinoxalinone-3-carbonyl chloride
P$^3$-[1-(4, 5-Dimethoxy-2-nitrophenyl)ethyl]adenosine-5'-tri-phosphate, trisodium salt P²-[1-(4, 5-Dimethoxy-2-nitrophenyl)ethyl]guanosine-5'-di-phosphate, disodium salt
P³-[1-(4, 5-Dimethoxy-2-nitrophenyl)ethyl]guanosine-5'-tri-phosphate, trisodium salt
4, 4'-Dimethoxytriphenylmethyl chloride
4-Dimethylaminoazobenzene-4'-isothiocyanate
N-[4-(6-Dimethylamino-2-benzofuranyl)phenyl]maleimide
9-Dimethyaminobenzo[α]phenoxazin-7-ium chloride
4-[4-(Dimethylamino)phenylazo]phenylisothiocyanate
5-(4-Dimethylaminophenyl)-2, 4-pentadienal
3-(2, 4-Dimethylanilinocarbonyl)-2-naphthol phosphate
3, 3'-Di(N-methyl-N-carboxymethyl)aminomethyl)-o-cresol-sulfonphthalein, sodium salt
Dimethyl-CFSE
3, 3'-Dimethyloxatricarbocyanine iodide
N, N-Dimethylformamide(Lu)
N, N-Dimethylformamide(Sp)
2, 9-Dimethyl-4, 7-diphenyl-1, 10-phenanthroline Table 15

2, 9-Dimethyl-4, 7-diphenyl-1, 10-phenanthrolinedisulfonic acid, disodium salt
2, 9-Dimethyl-1, 10-phenanthroline
2, 9-Dimethyl-o-phenanthroline
Dimethyl-POPOP(Sc)
Dimethylsulfonazo-M
Dimethyl sulfoxide(Lu)
Dimethyl sulfoxide(Sp)
3-(4, 5-Dimethyl-2-thiazolyl)-2, 5-diphenyl-2H-tetrazolium bromide
1, 2-Dimyristoylamide-1, 2-deoxyphosphatidyl choline
3-(2, 4-Dinitroanilino)-3'-amino-N-methyldipropylamine, dihydrochloride, hemihydrate
3, 5-Dinitrobenzoyl chloride
2, 2'-Di-p-nitrophenyl-5, 5'-diphenyl-3, 3'-dimethoxy-4, 4'-diphenylenediitetrazolium chloride
Dinitrosulfonazo-M
4'-(2", 6"-Dinitro-4-trifluromethylphenyl)aminobenzo-15-crown-5
4'-(2", 4"-Dinitro-6-trifluromethylphenyl)aminobenzo-15-crown-5
4, 16-Di-N-octadecylcarba moyl-3-oxabutyryl-1, 7, 10, 13, 19-pentaoxa-4, 16-diazacyclohenicosane
Di-n-octylphenylphosphonate
Dioxane(NS)
Dioxane(Sp)
Dioxane(Sc)
5-or6-(Dipalmitoylphosphatidylethanolcarbamoyl)-3', 6'-O, O-bis(2-nitrobenzyl)fluorescein, sodium salt
4, 7-Diphenyl-2, 9-dimethyl-1, 10-phenanthroline
4, 7-Diphenyl-2, 9-dimethyl-1, 10-phenanthrolinedisulfonic acid, disodium salt
Diphenylmethane-4, 4'-disulfonyl chloride
2, 5-Diphenyloxazole
4, 7-Diphenyl-1, 10-phenanthroline
4, 7-Diphenyl-1, 10-phenanthrolinedisulfonic acid, disodium salt
Diphenyl phoshorochloridate
5, 6-Diphenyl-3-(2-pyridyl)-1, 2, 4-triazine
1, 3-Diphenyl-2-thiobarbituric acid
Dipivaloylmethane
DIPSO
1, 3-Di(1-pyrenyl)propane
2, 2'-Dipyridyl
α, α'-Dipyridyl
Disodium Creatinephospate
N-[3-(1, 5-Disodiumsulfonaphthyl)]-N'-[4-(2, 2, 6, 6-tetramethylpiperidine-N-oxide)]thioureamethylpiperidene-N-oxide)]thiourea Table 16

2, 2'-Disulfo-4, 4'-diaminostilbene-N, N, N', N'-tetraacetic acid, disodium salt
N-[3-(1, 5-Disulfonaphthyl)]-N'-[4-(2, 2, 6, 6-tetramethylpiperidine-N-oxide)]thiourea, disodium salt
N-(Dithiocarboxy)sarcosine, diammonium salt
1, 3-Di-tert-butyl-1, 3-propanedione
2, 2'-Dithiobis(1-aminonuphthalene)
4, 4'-Dithiobis(1-azidobenene)
5, 5'-Dithiobis(2-nitrobenzoic acid)
2, 2'-Dithiobis(5-nitropyridine)
4, 4'-Dithiobisphenylazide
6, 6'-Dithio-di-2-naphthol
2, 2-'-Dithiodipyridine
4, 4'-Dithiodipyridine
1, 4-Dithiothreitol
DMEQ-COCI
DMSO(Sp)
DMTr-CI
D-myo-Inositol-1, 3, 4, 5-tetraphosphate, tetrapotassium salt
D-myo-Inositol-1, 4, 5-triphosphate, tripotassium salt
DNBC
Docosyl acridinium TCNQ salt
Docosyl alcohol
Docosyl pyridinium TCNQ salt
1, 11-Dodecadiyne
5, 7-Dodecadiyne-1, 12-diol bis(N-benzcarbamate)
5, 7-Dodecadiyne-1, 12-diol bis(N-ethylcarbamate)
5, 7-Dodecadiyne-1, 12-diol
n-Dodecyl-β-D-maltopyranoside
n-Dodecyl-β-D-maltoside
4-Dodecyloxy-4'-(3-carboxytrimethyleneoxy)azobenzene
Dodecylmethyl-bis(15-crown-5)
DOPP
DOC(Laser dye)
DODC(Laser dye)
DOTC(Laser dye)
tma-DPH
DPM
DPMDS
DPO
DPP
DPTA-OH
DPTBA
Drynap$^R$
DTAN
DTBPA
DTC(Laser dye)
DTCS
DTDC(Laser dye)
DTNB Table 17

DTPA
DTPA anhydride
DTTC(Laser dye)
EBT
ECDI
EDAC
EDC
EDDA
EDDP
EDDPO
EDTA disodium salt
EDTA 2Na salt
EDTA 3Na salt
EDTA 4Na salt
EDTA, 2NaBa salt EDTA, NaBi salt
EDTA, 2NaCa salt
EDTA, 2NaCo salt
EDTA, 2NaCu salt
EDTA, NaFe salt
EDTA, NaLa salt
EDTA, 2NaMg salt
EDTA, 2NaMn salt
EDTA, 2NaNi salt
EDTA, 2NaPb salt
EDTA, 2NaZn salt
EDTA-OH
EDTA tetrasodium salt
EDTA trisodium salt
EDTPO
EGS
EGTA
Electron carriers
Ellman's fReagents
EMCS
nzymatic Redox Indicators
EPPS
Eriochromazurol S
Eriochrome Black T
ETA
ETA-Acid
ETA-4NA
N,N'-1,2-Ethanediylbisglycine
2,2'-(Ethanediylidenedinitrilo)diphenol
N-Ethoxycarbonylmethyl-6-methoxyquinolinium bromide
Ethyl acetate(Sp)
Ethyl-CDI
Table 18
1-Ethyl-3-(3-dimethylaminopropyl)carbodiimide hydrochloride
N-Ethyl-N'-(3-dimethylamino)propylcarbodiimide hydrochloride
[Ethylenebis[(carboxymethyl)imino]ethylenenitrilo]-tetraacetic acid
Ethylenebis(iminodiacetic acid)
[Ethylene-bis(oxyethylenenitrilo]tetraacetic acid
Ethylenechloride(Sp)
Ethylenediamine-N,N'-diacetic acid
Ethylenediamine-N,N'-dipropionic acid hydrochloride
Ethylenediamine-N,N,N',N'-tetraacetic acid
Ethylenediamine-N,N,N',N'-tetraacetic acid,dipotassium salt
Ethylenediamine-N,N,N',N'-tetraacetic acid,tripotassium salt
Ethylenediamine-N,N,N',N'-tetraacetic acid, dilithium salt
Ethylenediamine-N,N,N',N'-tetraacetic acid, disodium salt
Ethylenediamine-N,N,N',N'-tetraacetic acid,trisodium salt
Ethylenediamine-N,N,N',N'-tetraacetic acid,tetrasodium salt
Ethylenediamine-N,N,N',N'-tetraacetic acid, diammonium salt
Ethylenediamine-N,N,N',N'-tetrakis-(methylenephosponic acid)
Ethylene dichloride(Sp)
N,N'-Ethylenediglycine
(Ethylenedinitrilo)diacetic acid
(Ethylenedinitrilo)tetraacetic acid
2,2'-Ethylenedioxybis[ethyliminodi(acetic acid)]
Ethyl Ether(Aq)
Ethyl Ether(AV,POV)
Ethyleneglycolbis(2-aminoethylether)-N,N,N',N'-tetraacetic acid
Ethyleneglycol-O, O'-bis(succinimidylsuccinate)
Ethyleneglycoldimethylether(Sc)
N-Ethyl-N-(2-hydroxy-3-sulfopropyl)aniline
N-Ethyl-N-(2-hydroxy-3-sulfopropyl)-m-anisidine
N-Ethyl-N-(2-hydroxy-3-sulfopropyl)-3,5-dimethylaniline
N-Ethyl-N-(2-hydroxy-3-sulfopropyl)-3,5-dimethoxyaniline
N-Ethyl-N-(2-hydroxy-3-sulfopropyl)-3-methoxyaniline, sodium salt,dihydrate
N-Ethyl-N-(2-hydroxy-3-sulfopropyl)-3-methylaniline, sodium salt,dihydrate
N-Ethyl-N-(2-hydroxy-3-sulfopropyl)-m-toluidine
N-Ethyl-N-sulfopropylaniline
N-Ethyl-N-sulfopropyl-m-anisidine
N-Ethyl-N-sulfopropyl-3,5-dimethylaniline
N-Ethyl-N-sulfopropyl-3,5-dimethoxyaniline
N-Ethyl-N-(3-sulfopropyl)-3-methoxyaniline,sodium salt, monohydrate
Eu-DPM(NMR)
Eu-FOD(NMR)
Eu-PTA(NMR)
Eu Tris(dipivaloylmethanate)
Eu Tris(heptafluorobutanoylpivaloylmethanate)
Table 19
Eu Tris(pivaloyltrifluoroacetonate)
Fast Blue VB
Fast Red ITR
5-F-BAPTA
5-F-BAPTA-AM
Fe(III)-AA
Fe(III)-CHBA(AS)
Fe(III)-EDTA
Ferric acetylacetonate
Ferrocenyl PEG
Ferrocenyl TMA
(11-Ferrocenyl)undecyltridecaethyleneglycol ether
(11-Ferrocenyl)undecyltrimethylammonium bromide
Ferro Ver
FITC(isomer-I)
Fluo 3
Fluo 3-AM
Fluoral-P
Fluoresceinbis(methyliminodiacetic acid)
Fluorescein isothiocyanate(isomer-I)
Fluoresceinmethyliminodiacetic acid
Fluorexone
4-Fluoro-7-nitrobenzofurazan
7-Fluoro-4-nitrobenzo-2-oxa-1,3-diazole
2-Fluoro-2-nitrodiphenyl ether
4-Fluoro-3-nitrophenylazide
4-Fluoro-7-sulfamoylbenzofurazan
7-Fluoro-4-sulfamoyl-2,1,3-benzoxadiazole
4-Fluoro-7-sulfobenzofurazan,ammonium salt
Fluostain I
Fluostain II
Fluostain III
Flu Ver
FNDPE
FNPA
Frost D
β-D-Fructopyranosyl-α-D-glucopyranoside monodecanoate
β-D-Fructopyranosyl-α-D-glucopyranoside monododecanoate
FTA
Fukugoo Tekiteieki(A)
Fukugoo Tekiteieki(B)
Fura 2
Fura 2-AM Fura 2-AM solution(1-mM)
2-Furildioxime
2-Furoyltrifluoroacetone
Table 20
GEDTA
GHA
GIETA
Glycinethymol Blue
Glycoletherdiaminetetraacetic acid
Glyoxalbis(2-hydroxyanil)
GMBS
Good's Buffers
Good's Butter Starter Kit
Good's Butter Solution
GTB
4H
HABT
HALPS
HBED
HBPHA
HDAOS
HDAPS
HDOPP-Ca
t-HDOPP-Ca
HDTA
BEEDTA
BEPES
HEPPS
HEPPSO
HEPS
Heptacosa-10,12-diynoic acid
16-Heptadecenoic acid
16-Heptadecynoic acid
Heptafluorobutanoylpivaloylmethane
1,1,1,2,2,3,3,-Heptafluoro-7,7-dimethyl-4,6-octanedione
n-Heptyl-β-D-thioglucoside
n-Heptane(Lu)
n-Heptane(Sp)
2,4-Hexadiyne-1,6-diol
2,4-Hexadiyne-1,6-diol dibenzoate
2,4-Hexadiyne-1,6-diol ditosylate
Hexafluoroacetylacetone
1,1,1,5,5,5-Hexafluoro-2,4-pentanedione
Hexamethylenediamino-N,N,N',N',-tetraacetic acid
1,3,3,1',3',3'-Hexamethylindocarbocyanine iodide
1,3,3,1',3',3'-Hexamethylindocarbodicyanine iodide
Hexanes(Lu)
Hexanes(Sp)
Table 21
Hexa Ver
HFA
HFPB
HHSNN
HIDA
HIC(Laser dye)
HIDC(Laser dye)
HMCS
HNB
HOBt
HOBt anhydrous
HO-EDTA
HPDTA
HPPA
HSN
Hyamine 10 X-OH
1-Hydroxy-1H-benzotriazole,monohydrate
1-Hydroxybenzotriazole anhydrous o-(o-Hydroxybenzylidene)aminophenol
N-[2-Hydroxy-1,1-bis(hydroxymethyl)ethyl]taurine
7-Hydroxycoumarin
2-Hydroxy-1,3-diaminopropane-N,N,N',N'-tetraacetic acid
2-(2-Hydroxy-3,6-disulfo-1-naphthylazo)benzenearsonic acid, disodium salt
2-Hydroxy-4-dodecyloxy-4'-(10-carboxydecamethyleneoxy)-salicylideneaniline
2-Hydroxy-4-dodecyloxy-4'-carboxysalicylideneaniline
2-Hydroxy-4-dodecyloxy-4'-(3-carboxytrimethyleneoxy)-salicylideneaniline
N-(2-Hydroxyethyl)ethylenediamin-N,N',N'-triacetic acid
N-(2-Hydroxyethyl)iminodiacetic acid
N-2-Hydroxyethylpiperazine-N'-2-ethanesulfonic acid
N-2-Hydroxyethylpiperazine-N'-2-hydroxypropane-3-sulfonic acid
N-2-Hydroxyethylpiperazine-N'-3-propanesulfonic acid
2-[4-(2-Hydroxyethyl)-1-piperazinyl]ethanesulfonic acid
3-[4-(2-Hydroxyethyl)-1-piperazinyl]propanesulfonic acid
2-Hydroxy-3-[4-(2-hydroxyethyl)-1-piperazinyl]-propanesulfonic acid, monohydrate
3-Hydroxy-4-[(1-hydroxy-4-methyl-2-phenyl)azo]-1-naphthalenesulfonic acid
2-Hydroxy-4-(2-hydroxy-5-methylphenylazo)-1-naphthalenesulfonic acid
3-Hydroxy-4-(1-hydroxy-2-naphthylazo)-7-nitro-1-naphthalenesulfonic acid, sodium salt
1-Hydroxy-2-(2-hydroxyphenylazo)benzene
Table 22
2-Hydroxy-1-(2-hydroxy-4-sulfo-1-naphthylazo)-3,6-naphthalenedisulfonic acid, trisodium salt
3-Hydroxy-4-[(2-hydroxy-4-sulfo-1-naphthyl)azo]-2,7-naphthalene-disulfonic acid trisodium salt
2-Hydroxy-1-(2-hydroxy-4-sulfo-1-naphthylazo)-3-naphthoic acid
3-Hydroxy-4-[(2-hydroxy-4-sulfo-1-naphthyl)azo]2-naphthoic acid
3-Hydroxy-4-[(o-hydroxyphenyl)azo-2-naphtho-2',4'-xylidine
3-Hydroxy-4-[(6-hydroxy-m-tolyl)azo]-1-naphthalene sulfonic acid
4-Hydroxy-3-((2-hydroxy-3-(2,4-xylidylcarbamoyl)-1-naphthylazo]benzenesulfonic acid sodium salt
{[(7-Hydroxy-4-methyl-2-oxo-2H-1-benzopyranyl)-8-methyl] imino}diacetic acid
1-(1-Hydroxy-4-methyl-2-phenylazo)-2-naphthol-4-sulfonic acid
2-Hydroxy-3-morpholinopropanesulfonic acid
Hydroxynaphthol Blue
3-Hydroxy-2-naphtho-2',4'-xylididedihydrogenphosphate
1-(1-Hydroxy-2-naphthylazo)-6-nitro-2-naphthol-4-sulfonic acid, sodium salt
[2-Hydroxy-5-(4-nitrophenylazo)phenyl]oxymethyl-15-crown-5
1-(2-Hydroxyphenylazo)-2-hydroxybenzene
o-N-(o-Hydroxyphenyl)formimidoylphenol
2-Hydroxyphenyl-1-(4,5-dimethoxy-2-nitrophenyl)-ethylphosphate,sodium salt
2-Hydroxyphenyl-1-(2-nitro-4,5-dimethoxy)-phenylethylphosphate,monosodium salt
2-Hydroxyphenyl-1-(2-nitrophenyl)ethylphosphate, sodium salt
3-(4-Hydroxyphenyl)propionic acid
8-Hydroxy-1-(salicylideneamino)-3,6-naphthalene-disulfonic acid,disodium salt
N,N'-{(α-Hydroxy-o-sulfobenzylidene)-bis[(6-hydroxy-5-isopropyl-2-methyl-m-phenylene)methylene]}diglycine, γ-sultone {(α-Hydroxy-o-sulfobenzylidene)bis{[(6-hydroxy-5-methyl-m-phenylene)methylene]nitrilo}}tetraacetic acid, γ-sultone, disodium salt
1-(2-Hydroxy-4-sulfonaphthylazo)-3,6-disulfonaphthalene, trisodium salt
o-{2-[α-(2-Hydroxy-5-sulfophenylazo)-benzylidene]hydrazino}-benzoic acid,sodium salt
N-(2-Hydroxy-3-sulfopropyl)-5-dimethoxyaniline
(2-Hydroxytrimethylene)dinitrilo-N,N,N',N'-tetraacetic acid
2-Hydroxy-N-tris(hydroxymethyl)methyl-3-aminopropanesulfonic acid
Table 23
IDA
Idranal I
Idranal II
Idranal in
Idranal IV
Idranal,V
iminodiacetic acid
N-[Imino (phosphonoamino) methyl]-N-methylglycine, disodium salt, tetrahydrate
Iminotriacetic acid
Indo 1
Indo 1-AM
Indo 1-AM solution
D,L-myvo-Inositol-1, 3, 4, 5-tetraphosphatea tetrapotassium salt
D-myo-Inositol-1, 4, 5-triphsphate, tripotassium salt
Ins (1, 4, 5) $P_3$ (synthetic)
Ins (1, 3,4, 5)$P_4$ (synthetic)
INT
2-(4-Iodophenyl)-3-(4-nitrophenyl)-5-(2,4-disulfophenyl)-2H-tatrazolium,monosodium salt
2-(4-Iodophenyl)-3-(2, 4-dinitrophenyl)-5-(2, 4-disulfophenyl)-2H-tetrazolium,monosodium salt
2-(4-Iodophenyl)-3-(p-nitrophenyl)-5-pheny-2H-tetrazolium chloride
Ionophores
Ionophore-K23E1
$IP_3$ (synthetic)
$IP_4$ (synthetic)
Ion Selective Electrodes
Isothiocyanobenzyl-EDTA
1-(4-Isothiocyanobenzyl)ethylenediamine-N,N,N',N'-tetraacetic acid
2K
3K
K-AA
Kalibor$^R$
Kalignost
Kanshoeki(pH 10)
α-Ketoglutaric acid
KMUS
Kobayashi's Peagent
Komplexon-I
Komplexon-II
Komplexon-III
Table 24
Koodo Tekiteieki(A)
Koodo Tekiteieki(B)
K-TCPB
La(III)-EDTA
Lauroyl sucrose
Lead cyclohexylbutyrate
Luminasol$^R$,(Lu)
Lumogallion
Lumogallion IREA
Magnesium cyclohexylbutyrate(for atom, absorp, standard)
Magnolet
Magon
Magon sulfonic acid
N-(4-Maleimidobutyryloxy)succinimide
N-(4-Maleimidobutyryloxy)sulfosuccinimide,sodium salt
N-(6-Maleimidocaproyloxy)succinimide
N-(6-Maleimidocaproyloxy)sulfosuccinimide,sodium salt
N-(8-Maleimidocapryloxy)succinimide
N-(8-Maleimidocapryloxy)sulfosuccinimide sodium salt
N-{[4-(2-Maleimidoethoxy)succinyl]oxy}succinimide
N-(11-Maleimidoundecanoyloxy)succinimide
N-(11-Maleimidoundecanoyloxy)sulfosuccinimide,sodium salt
Maleimido-$C_3$-benzyl-EDTA
Maleimido-$C_5$-benzyl-EDTA
3-O-{3'-[N-(N'-Maleimido)methylcarbonyl-N-carboxymethyl-amino]-3-aza-2-propenyl}-6-O-(2-nitrobenzyl)-fluorescein
1-[4-(5-Maleimidopentyl)amidobenzyl]ethylene-diamine-N,N,N',N'-tetraacetic acid
1-[4-(3-Maleimidopropyl)amidobenzyl]ethylene-diamine-N,N,N',N'-tetraacetic acid
Manganic acetylacetonate
Manganon
Manganous acetylacetonate
Manganous-CHBA(for atom, absorp, standard)
Man Ver
Table 25
Mannan derivative
Mann Reagent
MAOS
MAPS
MBD
MBPM
MDB
Meares' Rengents
MEGA-8
MEGA-9
MEGA-10
Meldola's Blue
2-Mercapto-4-phenyl-1,3,4-thiazoline-5-thione,potassium salt
5-Mercapto-3-phenyl-1,3,4-thiadiazole-2-thione, potassium salt
5-Mercapto-3-phenyl-2-thio-1,3,4-thiadiazolone potassium salt
3-Mercaptopropionic acid
8-Mercaptoquinoline hydrochloride
MES
MESS
Metal-CHBA
Metal-EDTA
Metal Indicators
Metallochromic Indicators
Metal Phthalein
4-(4-Methoxybenzylamino)-7-nitrobenzofurazan
7-(p-Methoxybenzylamino)-4-nitrobenzoxadiazole
1-Methoxy-N-methylphenazinium methylsulfate
1-Methoxyphenazinemethosulfate
N-(p-Methoxyphenyl)-p-phenylenediamine hydrochloride
1-Methoxy PMS
N-(6-Methoxyquinolyl)acetoethyl ester bromide
6-Methoxy-N-(3-sulfopropyl)quinolium,monohydrate
4-Methoxytriphenylmethyl chloride
Methylbenzethonium hydroxide
Methylcyclohexane(Sp)

Methyldodecyl-bis(15-crown-5)
Methyl-EDTA
4,4-Methylenebis(2,3-dimethy-1-phenyl-3-pyrazolin-5-one) monohydrate
4,4'-Methylenediantipyrine
N-[4-(5,6-Methylenedioxy-2-benzofuranyl)phenyl] maleimide
2,2'-(Methylidynenitrilo)diphenol
10-Methyl-9-(phenoxycarbonyl)acridinium fluorosulfonate
Table 26
10-Methyl-9-{4-[2-(succinimidyloxycarbonyl)ethyl]-phenyloxycarbonyl}acridinium fluorosulfonate
4-Methyl-5-(sulfomethylamino)-2-(2-thiazolylazo)benzoic acid
Methylsulfonazo-III
Methylthymol Blue
Methylthymol Blue Complexone
4-(β-Methylumbelliferonemethyleneiminodiacetic acid
Methylxylenol Blue
Mg(II)-CHBA (AS)
Mg(II)-EDTA
Mg-1dranal
MMTr-Cl
Mn(II)-AA
Mn(III)-AA
Mn(II)-CHBA(AS)
Mn(II)Cyclohexanebutyrate
Mn(II)Cyclohexylbutyrate
Mn(II)-EDTA
4-Monomethoxytriphenylmethyl chloride
$MoO_2$(II)-AA
MOPS
MOPSO
2-Morpholinoethanesulfonic acid,monohydrate
3-(N-Morpholino)-2-hydroxy-1-propanesulfonic acid
3-Morpholinopropanesulfonic acid
3-(N-Morpholino)propanesulfonic acid
N-Morphorino syndnonium,hydrochloride
MQAE
MS-NT
MTB
MTT
Murexide
MX(Murexide diluted with $K_2SO_4$)
MXB
d,1-myo-Inositol-1,3,4,5-tetraphosphate tetrapotassium salt
d-myo-Inositol-1,4,5-triphosphate tripotassium salt
Myristyldimethylbenzylammonium chloride
2NA
3NA
4NA
Na-AA
Na Bicinchoninate
Na-CHBA(AS)
NAM
NANA
Naphthalene(Sc)
Naphthalene-2,3-diamine
Table 27
1-(2,3-Naphthalenedicarboximidyl)propionyl fluoride
Naphtharson
Naphthazarin
Naphthol AS-MX phosphoric acid
NB-01
NB-02
NBD-Cl
NBD-F NBDI
NBHA
NC-04
NC-06
NC-11
Neocuproine
Neocuproine hemihydrate
Neoniclon
Neo-TB
Neo-Tetrazolium Blue
Neo-Thorin
New Norimax
$2NH_4$
Ni(II)-AA
Ni(II)-CHBA(AS)(for atom, absorp, standard)
Nickel acetylacetonate
Nickel cyclohexylbutyrate(for atom, absorp, standard)
Ni-EDTA
NIPF
NIR-1
NIR-2
Nitr 5
Nitr 7
5,5'-Nitrilodibarbituric acid, ammonium salt
Nitrilotriacetic acid
Nitrilotri(methylenephosphoric acid)
Nitrilotripropionic acid
o-Nitrobenzenearsonic acid
4"-Nitrobenzene-1",4-diazoamino-1,1'-azobenzene-2"-arsono-4"-sulfonic acid,sodium salt
O-p-Nitrobenzyl-N,N'-diisopropylisourea
O-(4-Nitrobenzyl)hydroxylamine hydrochloride
Nitro-BT
Nitrochromeazo
$P^3$-[1-(2-Nitro-4,5-dimethoxyphenyl)ethyl]adenosine 5'-triphosphate,trisodium salt
$P^2$[1-(2-Nitro-4,5-dimethoxyphenyl)ethyl]guanosine diphosphate disodium salt
$P^3$-[1-(2-Nitro-4,5-dimethoxyphenyl)ethyl]guanosine 5'-triphosphate trisodium salt
Nitro-ferroin
Nitroorthanilic S
Table 28
Nitro-PAPS
5-Nitro-2-PDS
5-Nitro-1,10-phenanthroline
o-Nitrophenylarsonic acid
Nitrophenylazo-15-crown-5
P-[1-(2-Nitrophenyl)ethyl]adenosine-3',5'-cyclic monophosphate
P-[1-(2-Nitroph,enyl)ethyl]guanosine-3',5'-cyclic monophosphate
$P^3$-[1-(2-Nitrophenyl)ethyl]adenosine-5'-triphosphate, sodium salt
$P^2$-[1-(2-Nitrophenyl)ethyl]guanosine-5'-diphosphate disodium salt
$P^3$-[1-(2-Nitrophenyl)ethyl]guanosine-5'-triphosphate trisodium salt
N-[1-(2-Nitrophenyl)ethyloxycarbonyl]-4-aminobutyric acid,sodium salt
N-1-[1-(2-Nitrophenyl)ethyloxycarbonyl]aspartic acid, monosodium salt
N-[1-(2-Nitrophenyl)ethyloxycarbonyl]glutamic acid, monosodium salt
N-[1-(2-Nitrophenyl)ethyloxycarbonyl]glycine, sodium salt
o-Nitrophenyloctyl ether
o-Nitrophenylphenyl ether 3'-Nitro-4'-picrylaminobenzo-18-crown-6
2-(5-Nitro-2-pyridylazo)-5-[N-propyl-N-(3-sulfopropyl) amino]-phenol disodium salt
S-Nitroso-N-acetyl penicillamine
Nitroso-ESAP
2-Nitroso-5-[N-ethyl-N-(3-sulfopropyl)amino]phenol
2-Nitroso-5-[N-propyl-N-(3-sulfopropyl)amino]phenol
Nitroso-PSAP
5-Nitro-2-[3-(4-p-sulfophenylazophenyl)-1-triazene]-benzenearsonic acid,sodium salt
Nitrosulfonazo-III
Nitro-TB
p-Nitro-TB
Nitro-Tetrazolium Blue
3'-Nitro-4'-(2,4,6-trinitrophenylamino)benzo-18-crown-6
NMR shift reagents
NN(Funmatsu)
NN(Junmatsu)
NN(Yooeki)
Nonacosa-10,12-diynoic acid
Nonadeca-2,4-diynoic acid
n-Nonanoyl-N-methylglucamide
Norimax
NP-05
NP-12
Table 29
NPOE
NPPE
NS-01
NS-02
NS-03
NS-04
NTA
NTB
NTP
NTPO
NU-03
Nullapon
3'-Nitro-4'-picrylaminobenzo-18-crown-6
OCPC
Octadecyl alcohol
Octadecyl acridinium TCNQ salt
N-Octadecyl-N-(9-acridyl)ammonium chloride
Octadecylpyridinium TCNQ salt
iso-Octane(Lu)
iso-Octane(Pr)
iso-Octane(Sp)
n-Octanoyl-N-methylglucamide
4-Octyl-4'-(5-carboxypentamethyleneoxy)azobenzene
4-Octyl-4'-(3-carboxytrimethyleneoxy)azobenzene
n-Octyl-β-D-glucopyranoside
n-Octyl-β-D-glucoside
n-Octyl-β-D-thioglucoside
Oligonucleotide Synthesis
OMB-COCI
ONPOE
Omega Chrome Black T
Organic Scintillators
Oxo-bis(2,4-pentanedionato)vanadium
α-Oxoglutaric acid
2-Oxo-1,5-pentanedioic acid
PAA
PACH
PAN
PAR
Patton & Reader's Indicator
Pb (II)-CHBA (AS)

Pb Cyclohexanebutyrate
Pb Cyclohexylbutyrate
Table 30
Pb(II)-EDTA
PBPB
PC
$PC_3$ P
2-PDS
4-PDS
PDT
PDTS
PEM
Pentacosa-10,12-diynoic acid
2,4-Pentanedione
Peptide Synthesis
Perma Klear-OH
o-Phenanthroline
1,10-Phenanthroline
Phenolphthalein-3,3'-bis(methyliminodiacetic acid)
Phenolphthalein Complexone
Phenylarsonic acid
3-Phenyl acetylacetone
N-Phenylbenzohydroxamic acid
N-phenylcinnamoyl hydroxamic acid
2,2'-p-Phenylenebis(5-phenyloxazole)
2,2'-p-Phenylenebis[5-(tolyl)oxazole]
3-Phenyl-5-mercapto-1,3,4-thiadiazole-2-thione,potassium salt
1-Phenyl-3-methyl-5-pyrazolone and 1-1'-diphenyl-3,3'-dimethyl-(4,4'-bipyrazoline)-5,5'-dione mixture
syn-Phenyl-2-pyridylketoxime
Phenyl-2-pyridylketoneoxime
4-Phenyl-5-thioketo-1,3,4-thiadiazole-2-thiol potassium salt
Phosphododecyl-14-crown-4
Phosphorylating Reagents
Photometric Reagents
Phthalein Complexone
Phthalein Purple
Phthalexon S
Picryaminocrown
Piperazine-1,4-bis-(2-ethanesulfonic acid)
Piperazine-1,4-bis-(2-hydroxy-3-propanesulfonic acid)
Piperazine-N,N'-bis-(2-ethanesulfonic acid)
Piperazine-N,N'-bis-(2-hydroxy-3-propanesulfonic acid)
N-[2-(1-Piperazinyl)ethyl]malemide,dihydrochloride
PIPES
Pivaloyltrifluroacetone
Plumbon
PMAC
Polychelate acid
Polytrop Blue B
PONALKIT$^R$(Analytical kits for water)
PONALKIT$^R$-ABS
PONALKIT$^R$-ABS refilling reagent
Table 31
PONALKIT$^R$-COD(for chemical oxygen demand)
PONALKIT$^R$-COD refilling reagent
PONALKIT$^R$-COD.L(for low chemical oxygen demand)
PONALKIT$^R$-COD.L refilling reagent
PONALKIT$^R$-CN.T(for total cyanide)
PONALKIT$^R$-CN.T refilling reagent
PONALKIT$^R$-CN.T.L(for low total cyanide)
PONALKIT$^R$-CN.T.L(refilling reagent color)reagent
PONALKIT$^R$-CN.T.L(refilling reagent)distiling reagent
PONALKIT$^R$-Cr.6(for Cr(W))refilling reagent
PONALKIT$^R$-Cr.6-II(for Cr(IV))
PONALKIT$^R$-Cr.6-II refilling reagent PONALKIT$^R$-Cr.T-II(for total Cr)
PONALKIT$^R$-Cr.T-II refilling reagent
PONALKIT$^R$-Cu(for Cu ion in water)
PONALKIT$^R$-Cu refilling reagent
PONALKIT$^R$-DO(for disolved oxygen in water)
PONALKIT$^R$-DO refilling reagent A,B,C
PONALKIT$^R$-DO refilling reagent D
PONALKIT$^R$-F(for F ion in water)
PONALKIT$^R$-F refilling reagent
PONALKIT$^R$-Fe(for Fe ion in water)
PONALKIT$^R$-Fe refilling reagent
PONALKIT$^R$-Ni(for Ni ion in water)
PONALKIT$^R$-Ni refilling reagent
PONALKIT$^R$-WH(for total hardness of water)
PONALKIT$^R$-WH(refilling reagent)A Powder
PONALKIT$^R$-WH(refilling reagent)B Tablets
Pontachrome Black TA
POPOP
Porphyrins
POPSO
Potassium acetylacetonate
Potassium carrier
Potassium tetrakis(p-chlorophenyl)borate
Potting Black C
PPC
PPKO
PPO
PR
Pr-DPM(NMR)
Pr-FOD(NMR)
Primasol$^R$
Propiolic acid
Pr-PTA(NMR)
Pr Tris(dipivaloylmethanate)
Pr Tris(heptafluorobutanoylpivaloylmethanate)
Pr Tris(pivaloyltrifluoroacetonate)
iso-Propanol(Lu)
iso-Propanol(Sp)
Table 32
iso-Propyl Alcohol(Lu)
iso-Propyl Alcohol(Sp)
1,2-Propylenediaminetetraacetic acid
1,2-Propylenedinitrilo-N,N,N',N',-tetraacetic acid
Protecting Reagents
p-Terphenyl(Sc)
PTA
Pullulan derivative
Pure Organic Solvents
Pyridine (NS)
1-(Pyridyl-2'-azo)-2-naphthol
4-(Pyridyl-2'-azo)resorcinol
2-(2-Pridylazo)chromotropic acid disodium salt
2-(2-Pridylazo)-1,8-dihydroxy-3,6-naphthalenedisulfonic acid, disodium salt
1-(2-Pyridylazo)-2-naphthol
4-(2-Pyridylazo)resorcinol
1-(2-Pyridylazo)-4-resorcinol
Purpuric acid, ammonium salt
PV
α-Pyridylazo-β-naphthol
3-(2-Pyridyl)-5,6-bis(4-sulfophenyl)-1,2,4-triazine, disodium salt
3-(2-Pyridyl)-5,6-diphenyl-1,2,4-triazine
Pyrocatechin violet
Pyrocatechol-3,5-disulfonic acid,disodium salt
Pyrocatecholsulfonphthalein
Pyrocatechol violet Pyrogallol Red
Pyrogallol sulfonphthalein
Quene 1
Quene 1-AM
Quick Test Kits
Quin 2
Quin 2-AM
Quin 2-AM solution(50mM)
Quinolinethiol
Redox Indicators
Rexenol (trisodium salt)
Rexene Fe$_3$(sodium salt)
Rexene Acid(free acid)
Rh (III)-AA
Rhod 2
Rhod 2-AM
Table 33
Rhodium acetylacetonate
SABF
Salicyl,aldehyde-2-oxyanil
1-(Salicylideneamino)-8-hydroxy-3,6-naphthalenedisulfonic acid
Salicylideneaminophenol
Salicylideneamino-2-thiophenol
Salicylideneaniline derivatives
Salicylidenediaminobenzofuran
SAPH
Sarcosine Cresol Red
SATP
SBD-Cl
SBD-F
Scintilamine$^R$-OH
Scintillator Cocktail
Scintisol$^R$
Scintisol$^R$500 (Universal scintillator cocktail)
Scintisol$^R$EX-H (Scintillator cocktail)
SCR
Sequestrene 138
Sequestrene AA
Sequestrene Na$_2$Ca
Sequestrene Na$_2$Co
Sequestrene Na$_2$Cu
Sequestrene Na$_3$
Shift Reagents (NMR)
SIN-1
Silver diethyldithiocarbamate
SM-1000
SM-1200
SNAP
SNPA
Sodium acetylacetonate
Sodium bicinchoninate
Sodium biphenyl(1M in Diglyme packed in vial)
Sodium carrier
Sodium cyclohexanebutyrate(for atom, absorp, standard)
Sodium cyclohexylbutyrate(for atom, absorp, standard)
Sodium tetrakis[3,5-bis(trifluoromethyl)phenyl]borate
Sodium tetrakis(p-fluorophenyl)borate
Sodium tetraphenylborate
Solochrome Brilliant Blue B
Solubilizers for membrane proteins
Solvent Extraction Reagents
SPADNS
Specialty Organic Materials
Table 34
Spectrosol$^R$
Spectrophotometric Reagents SPQ
Sr(II)-AA
Sr(II)-CHBA(AS)(for atom. absorp. standard)
Sr Cyclohexanebutyrate(for atom. absorp. standard)
Sr Cyclohexylbutyrate(for atom. absorp. standard)
Stilbazo
Stilbene-4,4'-bis(1-azo-3,4-dihydroxy-benzene)-2,2'-disulfonate,diammonium salt
Stilbenefluoblue SR
Stilbexon
STTA
Succinimidyl 4-bromomethyl-3-nitrobenzoate
Succinimidyl 4-(4-bromomethyl-3-nitrobenzoyl)-aminobutylate
Succinimidyl 6-(4-bromomethyl-3-nitrobenzoyl)-aminohexanoate
N-Succinimidyl-4-maleimidobutyrate
N-Succinimidyl-6-maleimidohexanoate
N-Succinimidyl-p-nitrophenylacetate
5-or6-(N-Succinimidyloxycarbonyl)-3',6'-O,O'-diacetylfluorescein
5-or6-(N-Succinimidyloxycarbonyl)-2',7'-dichloro-3',6'-O,O'-diacetylfluorescein
5-or6-(N-Succinimidyloxycarbonyl)-4',5'-dimethyl-3',6'-O,O'-diacetylfluorescein
4-(2-Succinimidyloxycarbonylethyl)phenyl-10-methylacridinium-9-carboxylate fluorosulfonate
5-or6-(N-Succinimidyloxycarbonylmethylcarbamonyl)-3', 6'-O,O'-bis(2-nitrobenzyl)fluorescein
Sucrose Monocaprate
Sucrose Monolaurate
Sulfarsazene
Sulfochlorophenol S
3-Sulfo-2,6-dichloro-3',3"-dimethyl-4'-hydroxyfuchsone-5, 5"-dicarboxylic acid,trisodium salt
Sulfo-EMCS
Sulfo-GMBS
Sulfo-HMCS
Sulfo-KMUS
N-[3-(1,5-Sulfonaphthyl)]-N'-[4-(2,2,6,6-Tetramethyl-1-piperidinooxy)]thiourea,disodium salt
Sulfonazo-III
Sulfongallein
2-(4-Sulfophenylazo)-1,8-dihydroxy-3,6-naphthalenedisulfonic acid,trisodium salt
2-(4-Sulfophenylazo)-4,5-dihydroxynaphthalene-2,7-disulfonic acid,trisodium salt
N-Sulfopropylaniline
Table 35
N-Sulfopropy-3,5-dimethoxyaniline
N-(3-Sulfopropyl)-3,3',5,5'-tetramethylbenzidine, sodium salt
Sulforhodamine 101 acid chloride
Sulfosuccinimidyl 4-(4-bromomethyl-3-nitrobenzoyl)-aminobutylate, sodium salt
Sulfosuccinimidyl 6-(4-bromomethyl-3-nitrobenzoyl)-aminohexanoate, sodium salt
5-or6-(N-Sulfosuccinimidyloxycarbonylmethylcarbamoyl)-3', 6'-O, O'-bis(2-nitrobenzyl)fluorescein, sodium salt
T
TAA
TAC
Takagi's Reagent
TAM
TAMB
TAMSMB
TAN
TAPM
TAPS
TAPSO
TAR
TB
TCNQ Li
Te
Tekiteieki (0.01M)
Tekiteieki (0.02M)
Tekiteieki (0.05M)
Tekiteieki (0.1M)
TEMPO-T
p-Terphenyl(Sc)
TES
3, 3', 4, 4'-Tetraaminobiphenyl, tetrahydrochloride
1, 11, 13, 23-Tetracosatetrayne
Tetracosyl alcohol
Tetradecyldimethylbenzylammonium chloride
Tetrahydrofuran(NS)
Tetrahydrofuran(Sp)
Tetrakis [3,5-bis( 1,1,1,3,3,3-hexafluoro-2-methoxy-2-propyl) phenyl]borate, sodium salt trihydrate
Tetrakis [3,5-bis(trifluoromethyl)phenyl]borate, sodium salt, dihydrate
Tetrakis(4-chlorophenyl)borate potassium salt
Tetrakis(4-fluorophenyl)borate, sodium salt, dihydrate
meso-5,10,15,20-Tetrakis [4-(1-methyl)-pyridinyl]21H, 23H-porphine, p-toluenesulfonate
Table 36
5,10,15,20-Tetrakis {4- [N-(trimethyl)ammonio] phenyl}-21H, 23H-porphine, p-toluenesulfonate
N, N, N', N'-Tetrakis(2-pyridylmethyl)ethylenediamine
Tetrakis(4-N-trimethylaminophenyl)porphine, p-toluenesulfonate
3,3',5,5'-Tetramethylbenzidine
3,3',5,5'-Tetramethylbenzidine, hydrochloride
3,3',5,5'-Tetramethyl [1,1'-biphenyl]-4,4'-diamine
[(p-1,1,3,3-Tetramethylbutylcresoxy)-ethoxyethyl] dimethyl-benzylammonium hydroxide
1,1,3,3-Tetramethylguanidine
2,2,6,6-Tetramethy-3,5-heptanedione
Tetramethylmurexide
meso-N-Tetramethylpyridylporphine, p-toluenesulfonate
2,2, 3,3-Tetramethyl-9-tetradecyl-1,4, 8,11-tetraoxacyclotetradecane
Tetraphenylarsonium chloride
Tetraphenylborate sodium salt
Tetraphenylboron Natrium
Tetraphenylphosphonium chloride
meso-Tetraphenylporphine
meso-5,10,15,20-Tetraphenyl-21H, 23H-porphine
5,10,15,20-Tetraphenyl-21H, 23H-porphinetetrasulfonic acid, disulfuric acid, tetrahydrate
meso-Tetraphenylporphine tetrasulfonate
meso-5,10,15,20-Tetraphenyl-21H, 23H-prophine tetrasulfonate
1H-Tetrazole
Tetrazolium Blue
Tetrazolium Salts
Tetrine Acid
Te Ver
Texas Red
4TF
6TF
TFPB
t-HDOPP-Ca
2-Thenoyltrifluoroacetone (2-Thenoyl)-ω, ω, ω-trifluoroacetone
6-(2-Thiazolylazo)-3-dimethylaminophenol
Thiazolyl Blue
2-(2-Thiazolylazo)-p-cresol
2-(2-Thiazolylazo)-5-dimethylamino-phenol
2-(2-Thiazolylazo)-5-dimethylamino benzonic acid
1-(2-Thiazolylazo)-2-naphthol
2-(2-Thiazolylazo)-4-methylphenol
4-(2-Thiazolylazo)-resorcinol
Thiooxine
Thio-2-TTA
Thorin
Thoron
Table 37
Thoronol
Thymolphthalein complexone
Thymolphthalexone
Thymolsulphonphthalein-3,3'-bis(methylaminoacetic acid)
Thymolsulphonphthalein-3,3'-bis(methyliminodiacetic acid)
ThymolSulfonphthalexon
Tillman's Reagent
TiO(II)-AA
Tiron
Titanyl acetylacetonate
Titra Ver
Titriplex-I
Titriplex-II
Titriplex-III
Titriplex-IV
Titrisol
Titri Ver
tma-DPH
TMBZ
TMBZ-HCl
TMBZ.PS
TMG
TMPyP
Toluene(Sc)
Toluene(Sp)
Toluene-3,4-dithiol, Zn chelate
TOPO
TOOS
TPAC
TPC
TPEN
TPM
TPP
TPPC
TPPS
TPTZ
trans-1,2-Diaminocyclohexane-N, N, N', N'-tetraacetic acid
1H-1,2,4-Triazole
Tricaprylmethylammonium chloride
Tricine
Tricosa-2,4-diynoic acid
Tricosa-10,12-diynoic. acid
22-Tricosenoic acid
22-Tricosynoic acid
N, N, N'-Triethyl-N'- [5-(N-succinimidyloxycarbonyl) pentyl]-9-cyanopyronine chloride
N, N, N'-Triethyl-N'-{5- [N"-(2-maleimidoethyl) piperazinocarbonyl)pentyl}-9-cyanopyronine chloride
Triethylenetetramine-N, N, N', N", N''', N'''-hexaacetic acid
Table 38
Trifluoroacetylacetone
4,4,4-Trifluoro-1-(2-furyl)-1,3-butanedione
1,1,1-Trifluoro-2,4-pentanedione
4,4,4-Trifluoro-1-phenyl-1,3-butanedione
1,1,1-Trifluoro-3-(2-thenoyl)-2-propanone
4,4,4-Trifluoro-1-(2-thienyl)-1,3-butanedione
Triglycollamic acid
Trifluoroacetylpivaloylmethane
1,1,1-Trifluoro-5,5-dimethyl-2,4-hexanedione
1,1,1-Trifluoro-4-mercapto-4-(2-thienyl)-3-butene-2-one
o-(4,5,6-Trihydroxy-3-oxo-3H-xanthen-9-yl) benzenesulfonic acid
Trilon A
Trilon B
Trimethylamine-α, α'α''-tricarboxylic acid
1-(4-Trimethylammoniumphenyl)-6-phenyl 1,3,5-hexatriene iodide
1-(2,4,6-Trimethylbenzenesulfonyl)-3-nitro-1H-1,2,4-triazole
2,2,4-Trimethylpentane(Lu)
2,2,4-Trimethylpentane(Pr)
2,2,4-Trimethylpentane(Sp)
4'-(2, 3,4-Trinitrophenyl)amino-5'-nitro-2, 3-benzo-1, 4, 7,10,13,16, -hexaoxacyclooctadecan-2-ene
18-(2, 3,4-Trinitrophenyl)amino-19-nitro-2, 3,5,6, 8,9,11, 12,14,15-decahydro-1,4, 7,10,13,16-benzohexaoxacyclooctadecene
Trioctylmethylammonium chloride
Tri-n-octylphosphine oxide
p-Triphenyl(Scintillator grade)
2,4,6-Tri-2-pyridyl-s-triazine
N-Tris(hydroxymethyl)methyl-3-aminopropanesulfonic acid
N- [Tris(hydroxymethyl)methyl]glycine
Tris(carboxymethyl)amine
Tris(dipivaloylmethanato)europium
Tris(dipivaloylmethanato)praseodymium
Tris(heptafluorobutanoylpivaloylmethanato)europium
Tris(heptafluorobutanoylpivaloylmethanato)praseodymium
N-Tris(hydroxymethyl)methyl-2-aminoethanesulfonic acid
3- [N-Tris(hydroxymethyl)methylamino]-2-hydroxy-1-propanesulfonic acid
N-Tris(hydroxymethyl)methyl-2-hydroxy-3-amino propanesulfonic acid
2,4,6-Tris(2-pyridyl)-1,3,5-triazine
Tris(pivaloyltrifluoroacetonato)europium
Tris(pivaloyltrifluoroacetonato)praseodymium
TTA
TTD-14-crown-4
TTHA
TTMAPP
Table 39
UBT
Umbellicomplexone
Umbelliferone
10-Undecenoic acid
10-Undecynoic acid
Universal BT (UBT)
Uranon
Vanadyl acetylacetonate
Vanadyl acetylacetonate(for atom, absorp, standard)
Variamine Blue B, Hydrochloride
Vinylenebis [3-sulfo-p-phenylene)nitrilo]tetraacetic acid
Versene
Versene Fe-3
Versene X 80
Versenol 120
VO(II)-AA
VO(II)-AA(AS) (for atom, absorp, standard)

VO(II)-EDTA
wsc
WST-1
WST-3
XB-I
XB-II
XO
Xylenylphthalein-bis-iminodiacetic acid
Xylenol Orange
Xylidyl Blue-I
Xylidyl Blue-II
Xylylazo VioletI
Zephiramine$_R$
Zephiran chloride
Zephirol
Table 40
Zinc acetylacetonate
Zincon
Zirconium acetylacetonate
Zn(II)-AA
Zn(II)-CHBA(AS)
Zn cyclohexanebutyrate (for atom, absorp, standard)
Zn cyclohexylbutyrate (for atom, absorp, standard)
Zn 3,4-dimercaptotoluene chelate
Zn-dithiol
Zn(II)-EDTA
Zn-Idranal
Zr (IV)-AA

Example-3

This invention makes it possible not only to discriminate the chemical situation of a molecule, but also to control the contrast of X-ray microscope imaging. Referring to the dependence on photon energy of absorption cross section accompanied with 1s →π* transition of benzene, FIG. 6 clearly indicates that the peak of absorption has a band width about 1eV. If the transmittance imaging is photographed by using X-ray source which is monochromed by one figures narrower band width than that of the resonance line and of which wavelength is variable, the contrast controlling is very easy. In this example, the case that the protein of tobacco mosaic virus is labelled by O-(4-Nitrobenzeyl) hydroxyamine as in Example-1 is estimated.

Figure 7:
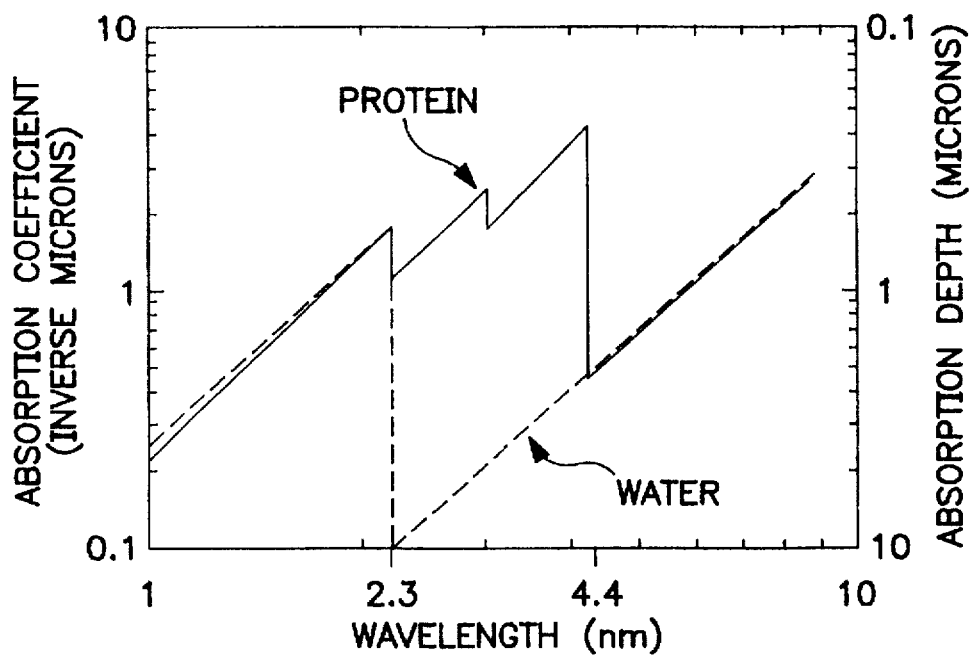
FIG. 7 is a graphic representation of absorption coefficient to the wave length of water and protein.

For instance, the spectro X-ray of band width about 50 meV having 285 eV around photon energy can be extracted by using "beam line PF-BL2" in Photon Factory of National Laboratory for High Energy Physics belonging to the Japanese Ministry of Education. When the tobacco mosaic virus labelled by leading value of photon energy of resonance line peak of 1s →π* transition is photographed by using said X-ray source, the contrast of around 0.1 can be obtained as illustrated in Example-1. If the said labelled tobacco mosaic virus is photographed using about 250 meV lower photon energy than the leading value of resonance line peak, the contrast is decreased to a half value because the absorption cross section becomes half. In the case of a biological cell bigger and including more protein than a tobacco mosaic virus, since the contrast is too strong, the observation of it's fine structure becomes impossible. In such a case, by using the X-ray microscopy of this invention, the contrast can be easily controlled by the selection of X-ray photon energy. On the other hand, when an X-ray photograph is taken by using the method based on inner shell ionizing absorption process at the wavelength region between 42.7Å and 23.6Å which is called as "water window", since it is clearly indicated in FIG. 7 that the variation in line absorption coefficient is moderate, the technique of this invention can not be applied. Therefore, the contrast is controlled by the thickness of a specimen, which needs a very complicated and skillful technique.

Example-4

The technique of this invention makes it possible to amplify the absorption effect to obtain an absorption imaging of a fine structure. When the density of chemical group to be observed is "N" and the X-ray absorption cross section of a labeller is "σχ", the line absorption coefficient "μ" is defined by formula (4).

$$\mu = N\sigma\chi \quad (4)$$

According to the formula (4), if the density "N" of a chemical group to be observed is small, it is very difficult to obtain an absorption imaging by the conventional method. However, in case of this invention, the said problem can be solved by molecule designing of a labeller.

Basically, an absorption cross section when inner shell electrons transit to π* orbit is directly proportional to the numbers of double bond which a labeller has. Therefore, by adding necessary numbers of side chain having double bond to the molecule of labeller, it become possible in proportion to improve the X-ray absorption cross sectional area of the labeller molecule. When the numbers of side chain to be added is "m" and X-ray absorption cross sectional area is "σχ", $$\sigma x = m\sigma s \quad (5)$$

Thus, the line absorption coefficient "μ" can be obtained by formula (6).

$$\mu = Nm\sigma s \quad (6)$$

For example, O-(4-Nitrobenzyl)hydroxylamine includes only one benzene ring which has double bond. However, concerning about a tobacco mosaic virus, when "m" number of benzene rings are added as a side chain, the line absorption coefficient is defined as formula (7).

$$\mu = m13/\mu m \quad (7)$$

Therefore, by adding five benzene rings, the contrast is increased to 0.5, and consequently the imaging of tobacco mosaic virus can be emphasized.

Example-5

According to the technique of this invention, the designing of a cell for a biological specimen becomes very easy. In general, because the light intensity of X-ray in the region used for a biological X-ray microscope is remarkably damped in the atmospheric air, whole system is usually contained in a vacuum cell. Therefore, the biological specimen of wet state is sealed up in a cell made of ultra thin film window so as not to be dried up in vacuum condition. Usually, in case of X-ray microscopy using photo ionization the materials which has excellent transmission for X-ray at wavelength region of "water window", and furthermore which can be easily processed to a thin film must be chosen as the material of an ultra thin film. And, in case of practical use of this invention, if an organic compound which does not include double bond is chosen as the material for said ultra thin film which has a high transmittance in the region of 280–290 eV and if a X-ray photograph is taken utilizing 1s →π* transition of carbon, the organic compound can be used as the material of high tenacious thin film.

Figure 9:
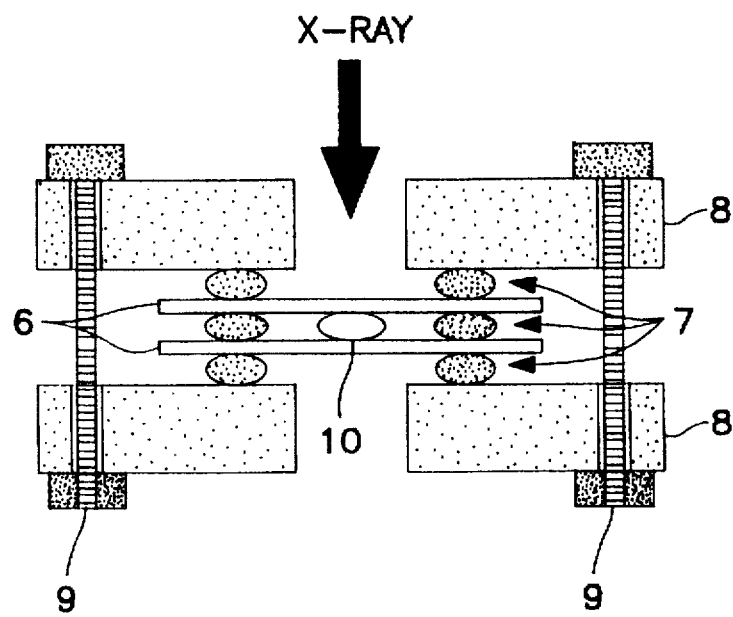
FIG. 9 is a longitudinal view of a cell for specimen observation.
Figure 10:
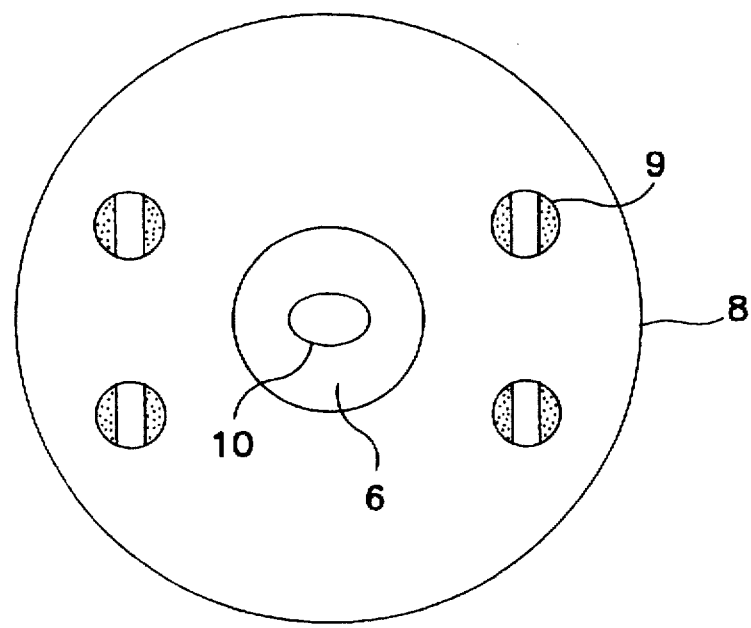
FIG. 10 is a plan view of a cell for specimen observation according to the invention.

FIG. 9 and FIG. 10 shows a longitudinal view and a plan view of a specimen container using polyethylene film (thickness: 0.12 μm, width: 5 mmø) for a X-ray microscope by inner shell excitation process. Polyethylene is a typical saturated highpolymer which does not include double bond, and consequently does not have a molecule orbit of π*. Therefore, it is expected that the polyethylene will indicate an excellent transmittance at the wavelength region between 44Å and 43.7Å (290–280 eV).

Figure 8:
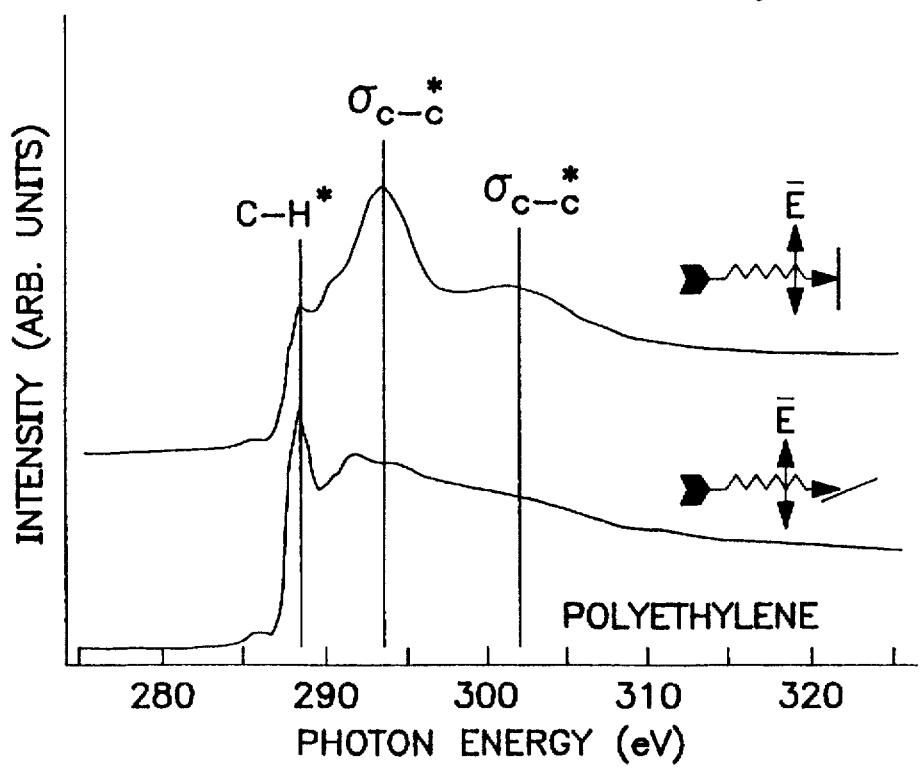
FIG. 8 is a graphic representation of photon energy to intensity of polyethylene.

FIG. 8 shows a feature of X-ray transmittance of polyethylene film actually measured by J. R. Rabe (J. R. Rabe et al: Thin Solid Films 159 [1998]275). It is clearly understood from FIG. 8 that the polyethylene film has an excellent transmittance at the photon energy below 287 eV. With respect to the microscopy which uses inner shell excitation process, considering the case to take a photograph of an absorption imaging of benzene ring of labeller which, has a strong absorption line at X-ray wavelength about 43.5Å (285 eV), the said film is the most suitable materials for the window of the specimen container.

The transmittance at 43.5Å (285 eV) of silicon nitride, the conventional material and that of polyethylene film is quantitatively compared. X-ray transmittance "T" can be indicated as follow, by using the line absorption coefficient "μ" and the thickness of window material "X".

$$T = \exp[-\mu X] \quad (8)$$

0.12 gm is applied to "X" and the value obtained from Henke's optical constant is applied to line absorption coefficient "μ". X-ray transmittance "T" obtained as the result for silicon nitride is 0.45, and for polyethylene film is over 0.95. In the case of polypropylene film, high X-ray transmittance can be obtained same as to the case of polyethylene film.

As above mentioned, it is clearly understood that carbon compounds which do not have π* orbit possess remarkably high X-ray coefficient. And it is also clearly understood by FIG. 9 and FIG. 10 that the structure of cell for a specimen using polyethylene film is very simplified. That is, two sheets of polyethylene film (6) is held by six O-rings (7), and a biological specimen (10) is set up between the space formed by two sheets of polyethylene film. Further, by using two upper and lower holders (8) and four screws (9), the space is sealed. Even if in vacuum condition, a biological specimen can be kept wet. And, in the process for preparing an ultra thin film window, since it is not necessary to use a complicated process such as anisotropic etching, the ultra thin film window and the cell for a specimen can be easily prepared by lower price.

As aforementioned, in the present invention, by using the monochromatic X-ray of lower photon energy than 2000 eV and of thinner wave length width than 1 eV, and especially by labelling of a specimen by a molecule including double bond, following high functional X-ray microscopy can be provided. Namely, the X-ray microscopy which can easily control the contrast by selection of photon energy of X-ray compared with the conventional X-ray microscopy using an inner shell ionization process.

What is claimed is:

1. In a method of observing a specimen with an X-ray microscope, the improvement comprising, labelling the specimen with a labelling molecule having a double bond prior to irradiating the specimen with X-rays.

2. The method according to claim 1, which further comprises irradiating the specimen with a monochromatic X-ray source of photon energy lower than 2000 eV with a band width narrower than 1 eV.

3. The method according to claim 2, wherein the monochromatic X-ray source has a variable wavelength with photon energy in the range between 280 eV and 550 eV.

4. The method according to claim 1, wherein said labelling molecule is a compound having a pentagonal or hexagonal ring.

5. The method according to claim 1, wherein said labelling molecule is a compound having a benzene ring.

6. The method according to claim 1, wherein said labelling molecule is a fluorescent pigment.

7. The method according to claim 1, further comprising containing said specimen in a container comprising an organic material not having a π* orbit and irradiating said specimen while in said container through said organic material.

8. The method according to claim 1, further comprising containing said specimen in a container comprising a carbonized compound which does not have a π* orbit and irradiating said specimen while in said container through said carbonized compound.

9. The method according to claim 1, wherein said labelling molecule further comprises a carbon atom, and wherein the step of irradiating the labelled specimen with X-rays results in absorption of the X-rays by and excitation of the is electron of the carbon atom to the π* orbit.

10. The method according to claim 1, wherein said labelling molecule further comprises a nitrogen atom, and wherein the step of irradiating the labelled specimen with X-rays results in absorption of the X-rays by and excitation of the Is electron of the nitrogen atom to the π* orbit.

11. The method according to claim 1, wherein said labelling molecule further comprises an oxygen atom, and wherein the step of irradiating the labelled specimen with X-rays results in absorption of the X-rays by and excitation of the is electron of the oxygen atom to the π* orbit.

12. The method according to claim 9, wherein the X-rays used to excite the is electron of carbon atom have a photon energy in the range of from 280 eV to 550 eV.

13. The method according to claim 10, wherein the X-rays used to excite the is electron of nitrogen atom have a photon energy in the range of from 280 eV to 550 eV.

14. The method according to claim 11, wherein the X-rays used to excite the is electron of oxygen atom have a photon energy in the range of from 280 eV to 550 eV.

15. The method according to claim 12, wherein the X-rays used to excite the is electron of carbon atom have a photon energy in the range of from 280 eV to 290 eV.

16. The method according to claim 1, wherein the specimen is a biological sample.

17. The method according to claim 16, wherein the X-rays used to irradiate the biological sample is not absorbed by water.

* * * * *

UNITED STATES PATENT AND TRADEMARK OFFICE
CERTIFICATE OF CORRECTION

PATENT NO. : 5,790,627
DATED : August 4, 1998
INVENTOR(S) : Yoshinori Iketaki

It is certified that error appears in the above-indentified patent and that said Letters Patent is hereby corrected as shown below:

```
Column 40, claim 10, line 5, change "Is" to --1s--;
           claim 11, line 5, change "is" to --1s--;
           claim 12, line 2, change "is" to --1s--;
           claim 13, line 2, change "is" to --1s--;
           claim 14, line 2, change "is" to --1s--;
           claim 15, line 2, change "is" to --1s--.
```

Signed and Sealed this

Twenty-ninth Day of December, 1998

Attest:

BRUCE LEHMAN

*Attesting Officer*  *Commissioner of Patents and Trademarks*